(12) United States Patent
Lopato et al.

(10) Patent No.: US 8,648,229 B2
(45) Date of Patent: Feb. 11, 2014

(54) PLANT SEED ACTIVE TRANSCRIPTIONAL CONTROL SEQUENCES

(75) Inventors: Sergiy Lopato, Morphett Vale (AU); Nataliya Kovalchuk, Brompton (AU); Ainur Ismagul, Myrtle Bank (AU); Jessica Anne Smith, Parkholme (AU)

(73) Assignee: Australian Centre for Plant Functional Genomics PTY Ltd, Urrbrae SA (AU)

( * ) Notice: Subject to any disclaimer, the term of this patent is extended or adjusted under 35 U.S.C. 154(b) by 629 days.

(21) Appl. No.: 12/677,771

(22) PCT Filed: Sep. 12, 2008

(86) PCT No.: PCT/AU2008/001359
§ 371 (c)(1),
(2), (4) Date: Jun. 11, 2010

(87) PCT Pub. No.: WO2009/033229
PCT Pub. Date: Mar. 19, 2009

(65) Prior Publication Data
US 2010/0287661 A1    Nov. 11, 2010

(30) Foreign Application Priority Data

Sep. 12, 2007    (AU) ................ 2007904960

(51) Int. Cl.
*C12N 15/00* (2006.01)
*C12N 15/82* (2006.01)
*C07H 21/04* (2006.01)
(52) U.S. Cl.
USPC .......... 800/278; 800/287; 435/468; 536/23.1; 536/24.1

(58) Field of Classification Search
None
See application file for complete search history.

(56) References Cited

U.S. PATENT DOCUMENTS

2004/0210043 A1*   10/2004   Abbitt et al. ................. 536/24.1
2007/0044171 A1*    2/2007   Kovalic et al. ................ 800/278

FOREIGN PATENT DOCUMENTS

WO    WO 98/08961 A2    3/1998
WO    WO98/08961    *    5/1998

OTHER PUBLICATIONS

Wu et al., Plant Cell Physiol. 39(8):885-89 (1998).*
Komarnytsky Genetic Engin_25_113_2003.*
Kim_Plant Mol Biol_24_105_1994.*
Donald_EMBO J_9_1717_1990.*
Dolferus_Plant Phys_105_1075_1994.*
GenBank Accession No. Z69631, "*H. vulgare* mRNA (clone END1)," 1 pg. (Feb. 19, 1996).
GenBank Accession No. BE402752, "CSB011C02F990908 ITEC CSB Wheat Endosperm Library *Triticum aestivum* cDNA clone CSB011C02, mRNA sequence," 2 pgs. (Jul. 21, 2000).

(Continued)

*Primary Examiner* — Shubo (Joe) Zhou
*Assistant Examiner* — Russell Boggs
(74) *Attorney, Agent, or Firm* — Klarquist Sparkman, LLP

(57) ABSTRACT

The present invention relates generally to transcriptional control sequences for effecting expression of a nucleotide sequence of interest in a plant. More particularly, the present invention relates to transcriptional control sequences that direct specific or preferential expression of an operably connected nucleotide sequence of interest in a plant seed or one or more particular cell or tissue types therein.

19 Claims, 5 Drawing Sheets

(56) References Cited

OTHER PUBLICATIONS

GenBank Accession No. BE602910, "HVSMEh0100N17f *Hordeum vulgare* 5-45 DAP spike EST library HVcDNA0009 (5 to 45 DAP) *Hordeum vulgare* subsp. *vulgare* cDNA clone HVSMEh0100N17f, mRNA sequence," 2 pgs. (Aug. 21, 2000).

GenBank Accession No. BF293667, "WHE2156_e11-i22zS *Triticum turgidum* L. var. *durum* (durum wheat) whole plant cDNA library *Triticum turgidum* cDNA clone WHE2156_e11_i22, mRNA sequence," 2 pgs. (Nov. 17, 2000).

GenBank Accession No. BG417716, "HVSMEk0019D22f *Hordeum vulgare* testa/pericarp EST library HVcDNA0013 (normal) *Hordeum vulgare* subsp. *vulgare* cDNA clone HVSMEk0019D22f, mRNA sequence," 2 pgs. (Oct. 23, 2001).

GenBank Accession No. BI947423, "HVSMEI0005H04f *Hordeum vulgare* spike EST library HVcDNA0012 (*Fusarium* infected) *Hordeum vulgare* subsp. *vulgare* cDNA clone HVSMEI0005H04f, mRNA sequence," 2 pgs. (Oct. 19, 2001).

GenBank Accession No. CA709282, "wdk2c.pk012.f21 wdk2c *Triticum aestivum* cDNA clone wdk2.c.pk012.f21 5-end,mRNA sequence," 2 pgs. (Nov. 26, 2002).

GenBank Accession No. CD906572, "G468.105C05F011012 G468 *Triticum aestivum* cDNA clone G468105C05, mRNA sequence," 1 pg. (Jul. 14, 2003).

GenBank Accession No. CI209767, "CI209767 *Oryza sativa* (japonica cultivar-group) same as Lib 33(supermix) *Oryza sativa* Japonica Group cDNA clone 038-M043R-E04 3-, mRNA sequence," 2 pgs. (Feb. 18, 2006).

GenBank Accession No. CV733912, "FLO—09-A16.b1 Rice flower lambda phage cDNA library (FLO) *Oryza sativa* Japonica Group cDNA clone FLO—09-A16, mRNA sequence," 2 pgs. (Nov. 5, 2004).

\* cited by examiner

PLANT SEED ACTIVE TRANSCRIPTIONAL CONTROL SEQUENCES

PRIORITY CLAIM

The present application is a U.S. National Stage Application of PCT/AU2008/001359, filed Sep. 12, 2008, which claims priority to Australian provisional patent application 2007904960, filed Sep. 12, 2007, the contents of which are herein incorporated by reference.

FIELD OF THE INVENTION

The present invention relates generally to transcriptional control sequences for effecting expression of a nucleotide sequence of interest in a plant. More particularly, the present invention relates to transcriptional control sequences that direct specific or preferential expression of an operably connected nucleotide sequence of interest in a plant seed or one or more particular cell or tissue types therein.

BACKGROUND OF THE INVENTION

The primary emphasis in genetic modification has been directed to prokaryotes and mammalian cells. For a variety of reasons, plants have proven more intransigent than other eukaryotic cells to genetically manipulate. However, in many instances, it is desirable to effect transcription of an introduced nucleotide sequence of interest in a plant.

Expression of a DNA sequence in a plant is dependent, in part, upon the presence of an operably linked transcriptional control sequence, such as a promoter or enhancer, which is functional within the plant. The transcriptional control sequence determines when and where within the plant the DNA sequence is expressed. For example, where continuous expression is desired throughout the cells of a plant, constitutive promoters are utilised. In contrast, where gene expression in response to a stimulus is desired, an inducible promoter may be used. Where expression in specific tissues or organs is desired, a tissue-specific promoter may be used.

Accordingly, there is a substantial interest in identifying transcriptional control sequences, such as promoters or enhancers, which are active in plants. Frequently, it is also desirable to specifically or preferentially direct transcription in particular plant organs, tissues or cell types, or at particular developmental stages of plant growth. Thus, isolation and characterisation of transcriptional control sequences, which can serve as regulatory regions for the expression of nucleotide sequences of interest in particular cell, tissues or organs of a plant, would be desirable for use in the genetic manipulation of plants.

Reference to any prior art in this specification is not, and should not be taken as, an acknowledgment or any form of suggestion that this prior art forms part of the common general knowledge in any country.

SUMMARY OF THE INVENTION

The present invention is predicated, in part, on the identification and functional characterisation of transcriptional control sequences which specifically or preferentially direct expression of an operably connected nucleotide sequence in a plant seed or one or more particular cell or tissue types therein.

Thus, in a first aspect, the present invention provides an isolated nucleic acid molecule comprising:
(i) a nucleotide sequence defining a transcriptional control sequence which specifically or preferentially directs expression of an operably connected nucleotide sequence in a plant seed, wherein said transcriptional control sequence is derived from a gene which encodes a polypeptide comprising the amino acid sequence set forth in SEQ ID NO: 1 or a homolog thereof; or
(ii) a nucleotide sequence defining a functionally active fragment or variant of the nucleotide sequence defined at (i).

As referred to herein, a plant "seed" should be understood to refer to a mature or immature plant seed. As such, the term "seed" includes, for example, immature seed carried by a maternal plant or seed released from the maternal plant. The term "seed" should also be understood to include any seed plant sporophyte between the developmental stages of fertilisation and germination.

The transcriptional control sequence or functionally active fragment or variant thereof may effect specific or preferential expression in a seed from at least one seed plant species. In some specific embodiments of the invention, the transcriptional control sequence specifically or preferentially directs expression of an operably connected nucleotide sequence in cereal crop plant seed, such as a wheat, rice or barley seed.

In one embodiment, the transcriptional control sequence is derived from a gene which comprises an open reading frame comprising the nucleotide sequence set forth in SEQ ID NO: 2 or a homolog thereof.

In another embodiment, the transcriptional control sequence contemplated by the first aspect of the invention comprises the nucleotide sequence set forth in SEQ ID NO: 3 or a functionally active fragment or variant thereof.

In a second aspect, the present invention also provides a nucleic acid construct comprising the isolated nucleic acid molecule of the first aspect of the invention.

In a third aspect, the present invention provides a cell comprising a nucleic acid construct of the second aspect of the invention.

The nucleic acid construct may be maintained in the cell as a nucleic acid molecule, as an autonomously replicating genetic element (e.g. a plasmid, cosmid, artificial chromosome or the like) or it may be integrated into the genomic DNA of the cell.

In a fourth aspect, the present invention contemplates a multicellular structure comprising one or more cells of the third aspect of the invention.

In one embodiment, the multicellular structure comprises a plant or a part, organ or tissue thereof, which in some embodiments may comprise a plant seed.

In some embodiments of the fourth aspect of the invention, a nucleotide sequence of interest may be operably connected to the transcriptional control sequence or the functionally active fragment or variant thereof, such that the nucleotide sequence of interest is specifically or preferentially expressed in a plant seed.

In a fifth aspect, the present invention provides a method for specifically or preferentially expressing a nucleotide sequence of interest in a plant seed, the method comprising effecting transcription of the nucleotide sequence of interest in a plant under the transcriptional control of the nucleic acid of the first aspect of the invention.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to herein by a sequence identifier number (SEQ ID NO:). A summary of the sequence identifiers is provided in Table 1. A sequence listing is provided at the end of the specification.

TABLE 1

Summary of Sequence Identifiers

| Sequence Identifier | Sequence | Sequence Listing Number |
| --- | --- | --- |
| SEQ ID NO: 1 | TdPR60 amino acid sequence | 400 <1> |
| SEQ ID NO: 2 | TdPR60 cDNA nucleotide sequence | 400 <2> |
| SEQ ID NO: 3 | TdPR60 promoter nucleotide sequence | 400 <3> |
| SEQ ID NO: 4 | TdPR60 genomic nucleotide sequence | 400 <4> |
| SEQ ID NO: 5 | BACW60R1 primer nucleotide sequence | 400 <5> |
| SEQ ID NO: 6 | BACW60R2 primer nucleotide sequence | 400 <6> |
| SEQ ID NO: 7 | BACW60R3 primer nucleotide sequence | 400 <7> |
| SEQ ID NO: 8 | BACW60R4 primer nucleotide sequence | 400 <8> |
| SEQ ID NO: 9 | BACW60R5 primer nucleotide sequence | 400 <9> |
| SEQ ID NO: 10 | BACW60R6 primer nucleotide sequence | 400 <10> |
| SEQ ID NO: 11 | BACW60R7 primer nucleotide sequence | 400 <11> |
| SEQ ID NO: 12 | BACW60R8 primer nucleotide sequence | 400 <12> |
| SEQ ID NO: 13 | pBACW60R9 primer nucleotide sequence | 400 <13> |
| SEQ ID NO: 14 | pBACW60R10 primer nucleotide sequence | 400 <14> |
| SEQ ID NO: 15 | C-BACW60a primer nucleotide sequence | 400 <15> |

Description Of Exemplary Embodiments

It is to be understood that the following description is for the purpose of describing particular embodiments only and is not intended to be limiting with respect to the above description.

The present invention is predicated, in part, on the identification and functional characterisation of transcriptional control sequences which specifically or preferentially direct expression of an operably connected nucleotide sequence in a plant seed or one or more particular cell or tissue types therein.

As used herein, the term "transcriptional control sequence" should be understood as a nucleotide sequence that modulates at least the transcription of an operably connected nucleotide sequence. As such, the transcriptional control sequences of the present invention may comprise any one or more of, for example, a leader, promoter, enhancer or upstream activating sequence. As referred to herein, the term "transcriptional control sequence" preferably at least includes a promoter. A "promoter" as referred to herein, encompasses any nucleic acid that confers, activates or enhances expression of an operably connected nucleotide sequence in a cell.

As used herein, the term "operably connected" refers to the connection of a transcriptional control sequence, such as a promoter, and a nucleotide sequence of interest in such a way as to bring the nucleotide sequence of interest under the transcriptional control of the transcriptional control sequence. For example, promoters are generally positioned 5' (upstream) of a nucleotide sequence to be operably connected to the promoter. In the construction of heterologous transcriptional control sequence/nucleotide sequence of interest combinations, it is generally preferred to position the promoter at a distance from the transcription start site that is approximately the same as the distance between that promoter and the gene it controls in its natural setting, i.e. the gene from which the promoter is derived. As is known in the art, some variation in this distance can be accommodated without loss of promoter function.

Thus, in a first aspect, the present invention provides an isolated nucleic acid molecule comprising:
(i) a nucleotide sequence defining a transcriptional control sequence which specifically or preferentially directs expression of an operably connected nucleotide sequence in a plant seed, wherein said transcriptional control sequence is derived from a gene which encodes a polypeptide comprising the amino acid sequence set forth in SEQ ID NO: 1 or a homolog thereof; or
(ii) a nucleotide sequence defining a functionally active fragment or variant of the nucleotide sequence defined at (i).

In the present invention, "isolated" refers to material removed from its original environment (e.g. the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. An "isolated" nucleic acid molecule should also be understood to include a synthetic nucleic acid molecule, including those produced by chemical synthesis using known methods in the art or by in-vitro amplification (e.g. polymerase chain reaction and the like).

The isolated nucleic acid molecule of the present invention may comprise any polyribonucleotide or polydeoxyribonucleotide, which may be unmodified RNA or DNA or modified RNA or DNA. For example, the isolated nucleic add molecules of the invention may comprise single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the isolated nucleic acid molecules may comprise triple-stranded regions comprising RNA or DNA or both RNA and DNA. The isolated nucleic acid molecules may also contain one or more modified bases or DNA or RNA backbones modified for stability or for other reasons. "Modified" bases include, for example, tritylated bases and unusual bases such as inosine. A variety of modifications can be made to DNA and RNA; thus the term "nucleic add" also embraces chemically, enzymatically, or metabolically modified forms of DNA and RNA.

As set out above, the method of the present invention contemplates a transcriptional control sequence which specifically or preferentially directs expression of an operably connected nucleotide sequence in a plant seed.

As referred to herein, a plant "seed" should be understood to refer to a mature or immature plant seed. As such, the term "seed" includes, for example, immature seed carried by a maternal plant or seed released from the maternal plant. The term "seed" should also be understood to include any seed plant sporophyte between the developmental stages of fertilisation and germination.

As would be appreciated, the term "seed" also encompasses the various cells and tissues that make up the mature or immature seed. For example, mature seeds may include tissue types such as the embryo, embryo surrounding region, endosperm transfer layer, starchy endosperm, aleurone layer, pericarp and the like. Meanwhile, immature seeds may include, for example, fertilised egg cells, zygotes, fertilised central cells, embryos, the endosperm coenocyte, the endosperm syncytium and the like.

It should be understood that reference herein to expression in a plant seed refers to the transcription and/or translation of a nucleotide sequence in one or more cells or tissues of a plant seed. This definition in no way implies that expression of the nucleotide sequence must occur in all cells of the plant seed.

As set out above, the transcriptional control sequences contemplated by the present invention "specifically or preferentially" direct expression of an operably connected nucleotide sequence in a plant seed. As used herein, "specifically expressing" means that the nucleotide sequence of interest is expressed substantially only in a plant seed or a particular tissue or cell type therein. "Preferentially expressing" should be understood to mean that the nucleotide sequence of interest is expressed at a higher level in a plant seed (or tissue or cell type therein) than in one or more other tissues of the plant, e.g. leaf tissue or root tissue. In some embodiments, preferential expression in a plant seed includes expression of a nucleotide sequence of interest in a plant seed at a level of at least twice, more preferably at least 5 times and most preferably at least 10 times the level of expression seen in at least one other tissue of the plant.

The transcriptional control sequence or functionally active fragment or variant thereof may effect specific or preferential expression in a seed from at least one seed plant species, including monocotyledonous angiosperm plants ('monocots'), dicotyledonous angiosperm plants ('dicots') and gymnosperm plants. For clarity, this should be understood as the transcriptional control sequence or functionally active fragment or variant thereof being able to effect specific or preferential expression in a seed in at least one seed plant species. The transcriptional control sequence may or may not effect expression in one or more other seed plant species, and this expression may or may not be specific or preferential to the seed. Thus, the transcriptional control sequences of the present invention need not be active in all seed plant species, and need not necessarily direct specific or preferential expression in the seed in all plants in which they are active.

In one embodiment, the transcriptional control sequence specifically or preferentially directs expression of an operably connected nucleotide sequence in a monocotyledonous plant seed.

In another embodiment, the transcriptional control sequence specifically or preferentially directs expression of an operably connected nucleotide sequence in a cereal crop plant seed.

As used herein, the term "cereal crop plant" may be a member of the Poaceae (grass family) that produces grain. Examples of Poaceae cereal crop plants include wheat, rice, maize, millets, sorghum, rye, triticale, oats, barley, teff, wild rice, spelt and the like. The term cereal crop plant should also be understood to include a number of non-Poaceae plant species that also produce edible grain, which are known as the pseudocereals and include, for example, amaranth, buckwheat and quina.

In another embodiment, the transcriptional control sequence specifically or preferentially directs expression of an operably connected nucleotide sequence in a wheat seed.

As referred to herein, "wheat" should be understood as a plant of the genus *Triticum*. Thus, the term "wheat" encompasses diploid wheat, tetraploid wheat and hexaploid wheat. In some embodiments, the wheat plant may be a cultivated species of wheat including, for example, *T. aestivum, T. durum, T. monococcum* or *T. spelta*. In one particular embodiment, the term "wheat" refers to wheat of the species *Triticum aestivum*.

In some embodiments, the transcriptional control sequence of the present invention may specifically or preferentially direct expression of an operably connected nucleotide sequence in one or more wheat seed tissues selected from the list consisting of: the endosperm transfer layer, the starchy endosperm and the aleurone tissue.

In further embodiments, the transcriptional control sequence may specifically or preferentially direct expression of an operably connected nucleotide sequence in a wheat seed, or one or more cell or tissue types therein, at least between 4 DAP and 13 DAP.

In another embodiment, the transcriptional control sequence specifically or preferentially directs expression of an operably connected nucleotide sequence in a barley seed.

As referred to herein, "barley" includes several members of the genus *Hordeum*. The term "barley" encompasses cultivated barley including two-row barley (*Hordeum distichum*), four-row barley (*Hordeum tetrastichum*) and six-row barley (*Hordeum vulgare*). In some embodiments, barley may also refer to wild barley, (*Hordeum spontaneum*). In one particular embodiment, the term "barley" refers to barley of the species *Hordeum vulgare*.

In some embodiments, the transcriptional control sequence of the present invention may specifically or preferentially direct expression of an operably connected nucleotide sequence in one or more barley seed tissues selected from the list consisting of: the endosperm transfer layer and the starchy endosperm.

In further embodiments, transcriptional control sequence may specifically or preferentially direct expression of an operably connected nucleotide sequence in a barley seed, or one or more cell or tissue types therein, at least between 11 DAP and 34 DAP.

In another embodiment, the transcriptional control sequence specifically or preferentially directs expression of an operably connected nucleotide sequence in a rice seed.

As referred to herein, "rice" includes several members of the genus *Oryza* including the species *Oryza sativa* and *Oryza glaberrima*. The term "rice" thus encompasses rice cultivars such as *japonica* or *sinica* varieties, *indica* varieties and *javonica* varieties. In one particular embodiment, the term "rice" refers to rice of the species *Oryza sativa*.

In some embodiments, the transcriptional control sequence of the present invention may specifically or preferentially direct expression of an operably connected nucleotide sequence in one or more rice seed tissues selected from the list consisting of: the starchy endosperm and the embryo surrounding region.

In further embodiments, transcriptional control sequence may specifically or preferentially direct expression of an operably connected nucleotide sequence in a rice seed, or one or more cell or tissue types therein, at least between 8 DAP and 47 DAP.

In further embodiments, the transcriptional control sequences of the present invention may also specifically or preferentially direct the expression of an operably connected nucleotide sequence in a dicotyledonous plant, or a seed, tissue or cell thereof. Exemplary dicots include, for example, *Arabidopsis* spp., *Nicotiana* spp., *Medicago* spp., soybean, canola, oil seed rape, sugar beet, mustard, sunflower, potato, safflower, cassava, yams, sweet potato, other *Brassicaceae* such as *Thellungiella halophila*, among others.

As set out above, the transcriptional control sequences of the present invention are derived from a gene which encodes a polypeptide comprising the amino add sequence set forth in SEQ ID NO: 1 or a homolog thereof.

The term "derived from", as used herein, refers to a source or origin for the transcriptional control sequence. For example, a transcriptional control sequence "derived from a gene which encodes a polypeptide comprising the amino acid sequence set forth in SEQ ID NO: 1" refers to a transcriptional control sequence which, in its native state, exerts at least some transcriptional control over a gene which encodes a polypeptide comprising the amino acid sequence set forth in SEQ ID NO: 1 in an organism. The term derived from should also be understood to refer to the source of the sequence information for a transcriptional control sequence and not be limited to the source of a nucleic acid itself. Thus, a transcriptional control sequence derived from a gene which encodes a polypeptide comprising the amino acid sequence set forth in SEQ ID NO: 1, need not necessarily be directly isolated from the gene. For example, a synthetic nucleic acid having a sequence that is determined with reference to a transcriptional control sequence which, in its native state, exerts at least some transcriptional control over a gene which encodes a polypeptide comprising the amino acid sequence set forth in SEQ ID NO: 1, should be considered derived from a gene which encodes a polypeptide comprising the amino acid sequence set forth in SEQ ID NO: 1.

The term "homolog", as used herein with reference to homologs of polypeptides comprising the amino acid sequence set forth in SEQ ID NO: 1, should be understood to include, for example, homologs, orthologs, paralogs, mutants and variants of polypeptides comprising the amino acid sequence set forth in SEQ ID NO: 1. In some embodiments, the homolog, ortholog, paralog, mutant or variant of a polypeptide comprising the amino acid sequence set forth in SEQ ID NO: 1 comprises an amino acid sequence which comprises at least 35% sequence identity, at least 40% sequence identity, at least 45% sequence identity, at least 50% sequence identity, at least 55% sequence identity, at least 60% sequence identity, at least 65% sequence identity, at least 70% sequence identity, at least 75% sequence identity, at least 80% sequence identity, at least 85% sequence identity, at least 90% sequence identity or at least 95% sequence identity to the amino acid sequence set forth in SEQ ID NO: 1.

When comparing amino acid sequences to calculate a percentage identity, the compared sequences should be compared over a comparison window of at least 20 amino acid residues, at least 40 amino acid residues, at least 60 amino acid residues, at least 80 amino acid residues, at least 100 amino acid residues, or over the full length of SEQ ID NO: 1. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms such the BLAST family of programs as, for example, disclosed by Altschul et al. (*Nucl. Acids Res.* 25: 3389-3402, 1997). A detailed discussion of sequence analysis can be found in Unit 19.3 of Ausubel et al. ("Current Protocols in Molecular Biology" John Wiley & Sons Inc, 1994-1998, Chapter 15, 1998).

The transcriptional control sequences of the present invention may be derived from any source, including isolated from any suitable organism or they may be synthetic nucleic acid molecules.

In one embodiment, however, the transcriptional control sequences contemplated herein are derived from a plant. In another embodiment, the transcriptional control sequences of the present invention are derived from a monocot plant species and in another embodiment, the transcriptional control sequences of the present invention are derived from a cereal crop plant species. In yet another embodiment, the transcriptional control sequence is derived from a *Triticum* species (for example *T. aestivum, T. durum, T. monococcum, T. dicoccon, T. spelta* or *T. polonicum*). In another embodiment, the transcriptional control sequence is derived from a tetraploid wheat (for example *T. durum, T. dicoccon,* or *T. polonicum*). In another embodiment, the transcriptional control sequence is derived from a durum wheat, and in yet another embodiment, the transcriptional control sequence is derived from *Triticum durum*.

In a further embodiment, the transcriptional control sequence is derived from a gene which comprises an open reading frame comprising the nucleotide sequence set forth in SEQ ID NO: 2 or a homolog thereof.

The term "homolog", as used herein with reference to homologs of genes comprising an open reading frame comprising the nucleotide sequence set forth in SEQ ID NO: 2, should be understood to include, for example, homologs, orthologs, paralogs, mutants and variants of genes comprising an open reading frame which comprises the nucleotide sequence set forth in SEQ ID NO: 2. In some embodiments, the homolog, ortholog, paralog, mutant or variant of a polypeptide comprising an open reading frame which comprises the nucleotide sequence set forth in SEQ ID NO: 2 comprises a nucleotide sequence which comprises at least 35% sequence identity, at least 40% sequence identity, at least 45% sequence identity, at least 50% sequence identity, at least 55% sequence identity, at least 60% sequence identity, at least 65% sequence identity, at least 70% sequence identity, at least 75% sequence identity, at least 80% sequence identity, at least 85% sequence identity, at least 90% sequence identity or at least 95% sequence identity to the nucleotide sequence set forth in SEQ ID NO: 2.

When comparing nucleotide sequences to calculate a percentage identity, the compared sequences should be compared over a comparison window of at least 20 nucleotide residues, at least 50 nucleotide residues, at least 100 nucleotide residues, at least 150 nucleotide residues, at least 200 nucleotide residues, at least 250 nucleotide residues or over the full length of SEQ ID NO: 2. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms such the BLAST family of programs as, for example, disclosed by Altschul et al. (*Nucl. Acids Res.* 25: 3389-3402, 1997). A detailed discussion of sequence analysis can be found in Unit 19.3 of Ausubel et al. ("Current Protocols in Molecular Biology" John Wiley & Sons Inc, 1994-1998, Chapter 15, 1998).

Methods for the derivation of a transcriptional control sequence from a gene in a plant or another organism are known in the art and the present invention contemplates the use of any such methods. In one example, a method such as "chromosome walking" (as described in Example 4) may be used to derive a promoter sequence from a gene. In a further example, where sequence data is available, a promoter may be derived in silico by searching for a promoter sequence upstream of a gene.

In a yet further embodiment, the transcriptional control sequence contemplated by the first aspect of the invention comprises the nucleotide sequence set forth in SEQ ID NO: 3 or a functionally active fragment or variant thereof.

As set out above, the present invention also contemplates "functionally active fragments or variants" of the transcriptional control sequences of the present invention, including (but not limited to) functionally active fragments or variants of a transcriptional control sequence comprising the nucleotide sequence set forth in SEQ ID NO: 3.

"Functionally active fragments" of the transcriptional control sequence of the invention include fragments of a transcriptional control sequence which retain the capability to specifically or preferentially direct expression of an operably connected nucleotide sequence in a plant seed (or a particular cell or tissue type thereof) in at least one plant type. In some embodiments of the invention the functionally active fragment is at least 200 nucleotides (nt), at least 500 nt, at least 1000 nt, at least 1500 nt or at least 2000 nt in length. In further embodiments, the fragment comprises at least 200 nt, at least 500 nt, at least 1000 nt, at least 1500 nt or at least 2000 nt contiguous bases from the nucleotide sequence set forth in SEQ ID NO: 3.

"Functionally active variants" of the transcriptional control sequence of the invention include orthologs, mutants, synthetic variants, analogs and the like which are capable of effecting transcriptional control of an operably connected nucleotide sequence in a plant seed (or a particular cell or tissue type thereof) in at least one plant type. The term "variant" should be considered to specifically include, for example, orthologous transcriptional control sequences from other organisms; mutants of the transcriptional control sequence; variants of the transcriptional control sequence wherein one or more of the nucleotides within the sequence has been substituted, added or deleted; and analogs that contain one or more modified bases or DNA or RNA backbones modified for stability or for other reasons. "Modified" bases include, for example, tritylated bases and unusual bases such as inosine.

In further embodiments, the functionally active fragment or variant comprises at least 50%, at least 55%, at least 60%, at least 65%, at least 70%, at least 75%, at least 80%, at least 82%, at least 85%, at least 87%, at least 90%, at least 92%, at least 95%, at least 96%, at least 97%, at least 98% or at least 99% nucleotide sequence identity to the nucleotide sequence set forth in SEQ ID NO: 3. When comparing nucleic acid sequences to calculate a percentage identity, the compared nucleotide sequences should be compared over a comparison window of at least 200 nucleotide residues, at least 400 nucleotide residues, at least 1000 nucleotide residues, at least 2000 nucleotide residues or over the full length of SEQ ID NO: 3. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms such the BLAST family of programs as, for example, disclosed by Altschul et al. (1997, supra). A detailed discussion of sequence analysis can be found in Unit 19.3 of Ausubel et al. (1998, supra).

In another embodiment, the functionally active fragment or variant comprises a nucleic acid molecule which hybridises to a nucleic acid molecule defining a transcriptional control sequence of the present invention under stringent conditions. In one embodiment, the functionally active fragment or variant comprises a nucleic acid molecule which hybridises to a nucleic acid molecule comprising the nucleotide sequence set forth in SEQ ID NO: 3 under stringent conditions.

As used herein, "stringent" hybridisation conditions will be those in which the salt concentration is less than about 1.5 M Na ion, typically about 0.01 to 1.0 M Na ion concentration (or other salts) at pH 7.0 to 8.3 and the temperature is at least 30° C. Stringent conditions may also be achieved with the addition of destabilising agents such as formamide. In some embodiments, stringent hybridisation conditions may be low stringency conditions, medium stringency conditions or high stringency conditions. Exemplary low stringency conditions include hybridisation with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridisation in 40 to 45% formamide, 1.0 M NaCl, 1% SDS at 37° C., and a wash in 0.5× to 1×SSC at 55 to 60° C. Exemplary high stringency conditions include hybridisation in 50% formamide, 1 M NaCl, 1% SDS at 37° C., and a wash in 0.1×SSC at 60 to 65° C. Optionally, wash buffers may comprise about 0.1% to about 1% SDS. Duration of hybridisation is generally less than 24 hours, usually 4 to 12 hours.

Specificity of hybridisation is also a function of post-hybridisation wash conditions, with the critical factors being the ionic strength and temperature of the final wash solution. For DNA-DNA hybrids, the $T_m$ can be approximated from the equation of Meinkoth and Wahl (*Anal. Biochem.* 138: 267-284, 1984), i.e. $T_m = 81.5°$ C. $+ 16.6$ (log M) $+ 0.41$ (% GC) $- 0.61$ (% form) $- 500/L$; where M is the molarity of monovalent cations, % GC is the percentage of guanosine and cytosine nucleotides in the DNA, % form is the percentage of formamide in the hybridisation solution, and L is the length of the hybrid in base pairs. The $T_m$ is the temperature (under defined ionic strength and pH) at which 50% of a complementary target sequence hybridises to a perfectly matched probe. $T_m$ is reduced by about 1° C. for each 1% of mismatching; thus, $T_m$, hybridisation, and/or wash conditions can be adjusted to hybridise to sequences of different degrees of complementarity. For example, sequences with ≥90% identity can be hybridised by decreasing the $T_m$ by about 10° C. Generally, stringent conditions are selected to be about 5° C. lower than the thermal melting point ($T_m$) for the specific sequence and its complement at a defined ionic strength and pH. However, high stringency conditions can utilise a hybridisation and/or wash at, for example, 1, 2, 3, or 4° C. lower than the thermal melting point ($T_m$); medium stringency conditions can utilise a hybridisation and/or wash at, for example, 6, 7, 8, 9, or 10° C. lower than the thermal melting point ($T_m$); low stringency conditions can utilise a hybridisation and/or wash at, for example, 11, 12, 13, 14, 15, or 20° C. lower than the thermal melting point ($T_m$). Using the equation, hybridisation and wash compositions, and desired $T_m$, those of ordinary skill will understand that variations in the stringency of hybridisation and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridisation of nucleic adds is found in Tijssen (*Laboratory Techniques in Biochemistry and Molecular Biology-Hybridisation with Nucleic Acid Probes*, Pt I, Chapter 2, Elsevier, N.Y., 1993), Ausubel et al., eds. (*Current Protocols in Molecular Biology*, Chapter 2, Greene Publishing and Wiley-Interscience, New York, 1995) and Sambrook et al. (*Molecular Cloning: A Laboratory Manual*, $2^{nd}$ ed., Cold Spring Harbor Laboratory Press, Plainview, N.Y., 1989).

In a second aspect, the present invention also provides a nucleic acid construct comprising the isolated nucleic acid molecule of the first aspect of the invention.

The nucleic acid construct of the second aspect of the present invention may comprise any polyribonucleotide or polydeoxyribonucleotide, which may be unmodified RNA or DNA or modified RNA or DNA. For example, the nucleic acid construct of the invention may comprise single- and/or double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the nucleic acid construct may comprise triple-stranded regions comprising RNA or DNA or both RNA and DNA. The nucleic acid construct may also comprise one or more modified bases or DNA or RNA backbones modified for stability or for other reasons. "Modified" bases include, for example, tritylated bases and unusual bases such as inosine. A variety of modifications can be made to DNA and RNA; thus the term "nucleic acid construct" embraces chemically, enzymatically, or metabolically modified forms.

In one embodiment, the nucleic acid construct comprises DNA. Accordingly, the nucleic acid construct of the present invention may comprise, for example, a linear DNA molecule, a plasmid, a transposon, a cosmid, an artificial chromosome or the like. Furthermore, the nucleic acid construct of the present invention may be a separate nucleic acid molecule or may be a part of a larger nucleic acid molecule.

In another embodiment, the nucleic acid construct further comprises a nucleotide sequence of interest that is heterologous with respect to the transcriptional control sequence or the functionally active fragment or variant thereof; wherein the nucleotide sequence of interest is operably connected to the transcriptional control sequence or functionally active fragment or variant thereof.

The term "heterologous with respect to the transcriptional control sequence" refers to the nucleotide sequence of interest being any nucleotide sequence other than that which the transcriptional control sequence (or functionally active fragment or variant thereof) is operably connected to in its natural state. For example, in its natural state, SEQ ID NO: 3 is operably connected to the nucleotide sequence set forth in SEQ ID NO: 4. Accordingly, in this example, any nucleotide sequence other than a nucleotide sequence consisting of the nucleotide sequence set forth in SEQ ID NO: 4 should be considered heterologous with respect to SEQ ID NO: 3. In accordance with the definition above, it would be recognised that a nucleotide sequence of interest which is heterologous to the transcriptional control sequence (or functionally active fragment or variant thereof) may be derived from an organism of a different taxon to the transcriptional control sequence (or functionally active fragment or variant thereof) or the nucleotide sequence of interest may be a heterologous sequence from an organism of the same taxon.

In yet another embodiment, the nucleic acid construct may further comprise a nucleotide sequence defining a transcription terminator. The term "transcription terminator" or "terminator" refers to a DNA sequence at the end of a transcriptional unit which signals termination of transcription. Terminators are generally 3'-non-translated DNA sequences and may contain a polyadenylation signal, which facilitates the addition of polyadenylate sequences to the 3'-end of a primary transcript. As with promoter sequences, the terminator may be any terminator sequence which is operable in the cells, tissues or organs in which it is intended to be used. Examples of suitable terminator sequences which may be useful in plant cells include: the nopaline synthase (nos) terminator, the CaMV 35S terminator, the octopine synthase (ocs) terminator, potato proteinase inhibitor gene (pin) terminators, such as the pinII and pinIII terminators and the like.

In one embodiment, the nucleic acid construct comprises an expression cassette comprising the structure:

$([N]_w\text{-TCS-}[N]_x\text{-SoI-}[N]_y\text{-TT-}[N]_z)$ wherein:
$[N]_w$ comprises one or more nucleotide residues, or is absent;
TCS comprises a nucleic acid of the first aspect of the invention;
$[N]_x$ comprises one or more nucleotide residues, or is absent;
SoI comprises a nucleotide sequence of interest which encodes an mRNA or non-translated RNA, wherein the nucleotide sequence, SoI, is operably connected to TCS;
$[N]_y$ comprises one or more nucleotide residues, or is absent;
TT comprises a nucleotide sequence defining a transcription terminator;
$[N]_z$ comprises one or more nucleotide residues, or is absent.

The nucleic acid constructs of the present invention may further comprise other nucleotide sequences as desired. For example, the nucleic acid construct may include an origin of replication for one or more hosts; a selectable marker gene which is active in one or more hosts or the like.

As used herein, the term "selectable marker gene" includes any gene that confers a phenotype on a cell, in which it is expressed, to facilitate the identification and/or selection of cells which are transfected or transformed with a nucleic acid construct of the invention. A range of nucleotide sequences encoding suitable selectable markers are known in the art. Exemplary nucleotide sequences that encode selectable markers include: antibiotic resistance genes such as ampicillin-resistance genes, tetracycline-resistance genes, kanamycin-resistance genes, the AURI-C gene which confers resistance to the antibiotic aureobasidin A, neomycin phosphotransferase genes (e.g. nptI and nptII) and hygromycin phosphotransferase genes (e.g. hpt); herbicide resistance genes including glufosinate, phosphinothricin or bialaphos resistance genes such as phosphinothricin acetyl transferase-encoding genes (e.g. bar), glyphosate resistance genes including 3-enoyl pyruvyl shikimate 5-phosphate synthase-encoding genes (e.g. aroA), bromyxnil resistance genes including bromyxnil nitrilase-encoding genes, sulfonamide resistance genes including dihydropterate synthase-encoding genes (e.g. sul) and sulfonylurea resistance genes including acetolactate synthase-encoding genes; enzyme-encoding reporter genes such as GUS-encoding and chloramphenicolacetyltransferase (CAT)-encoding genes; fluorescent reporter genes such as the green fluorescent protein-encoding gene; and luminescence-based reporter genes such as the luciferase gene, amongst others.

The genetic constructs described herein may further include nucleotide sequences intended for the maintenance and/or replication of the genetic construct in prokaryotes or eukaryotes and/or the integration of the genetic construct or a part thereof into the genome of a eukaryotic or prokaryotic cell.

In one embodiment, the construct of the invention is adapted to be at least partially transferred into a plant cell via *Agrobacterium*-mediated transformation. Accordingly, in one specific embodiment, the nucleic acid construct of the present invention comprises left and/or right T-DNA border sequences. Suitable T-DNA border sequences would be readily ascertained by one of skill in the art. However, the term "T-DNA border sequences" should be understood to include, for example, any substantially homologous and substantially directly repeated nucleotide sequences that delimit a nucleic acid molecule that is transferred from an *Agrobacterium* sp. cell into a plant cell susceptible to *Agrobacterium*-mediated transformation. By way of example, reference is made to the paper of Peralta and Ream (*Proc. Natl. Acad. Sci. USA*, 82(15): 5112-5116, 1985) and the review of Gelvin (*Microbiology and Molecular Biology Reviews*, 67(1): 16-37, 2003).

In further preferred embodiments, the present invention also contemplates any suitable modifications to the genetic construct which facilitate bacterial mediated insertion into a plant cell via bacteria other than *Agrobacterium* sp., for example, as described in Broothaerts et al. (*Nature* 433: 629-633, 2005).

Those skilled in the art will be aware of how to produce the constructs described herein, and of the requirements for obtaining the expression thereof, when so desired, in a specific cell or cell-type under the conditions desired. In particular, it will be known to those skilled in the art that the genetic manipulations required to perform the present invention may require the propagation of a genetic construct described herein or a derivative thereof in a prokaryotic cell such as an *E. coli* cell or a plant cell or an animal cell. Exemplary methods for cloning nucleic acid molecules are described in Sambrook et al. (*Molecular Cloning: A Laboratory Manual*, Cold Spring Harbor Laboratory Press, New York, 2000).

In a third aspect, the present invention provides a cell comprising a nucleic acid construct of the second aspect of the invention.

The nucleic acid construct may be maintained in the cell as a nucleic acid molecule, as an autonomously replicating genetic element (e.g. a plasmid, cosmid, artificial chromosome or the like) or it may be integrated into the genomic DNA of the cell.

As used herein, the term "genomic DNA" should be understood in its broadest context to include any and all endogenous DNA that makes up the genetic complement of a cell. As such, the genomic DNA of a cell should be understood to include chromosomes, mitochondrial DNA, plastid DNA, chloroplast DNA, endogenous plasmid DNA and the like. As such, the term "genomically integrated" contemplates chromosomal integration, mitochondrial DNA integration, plastid DNA integration, chloroplast DNA integration, endogenous plasmid integration, and the like. A "genomically integrated form" of the construct may be all or part of the construct. However, in one particular embodiment the genomically integrated form of the construct at least includes the nucleic acid molecule of the first aspect of the invention.

The cells contemplated by the third aspect of the invention include any prokaryotic or eukaryotic cell. In one embodiment, the cell is a plant cell. In another embodiment the cell is a monocot plant cell. In yet another embodiment the cell is a cereal crop plant cell and in one particular embodiment the cell is a wheat cell. In another particular embodiment the cell is a barley cell. In yet another particular embodiment the cell is a rice cell.

In another embodiment, the cell may also comprise a prokaryotic cell. For example, the prokaryotic cell may include an *Agrobacterium* sp. cell (or other bacterial cell), which carries the nucleic acid construct and which may, for example, be used to transform a plant. In another exemplary embodiment, the prokaryotic cell may be a cell used in the construction or cloning of the nucleic acid construct (e.g. an *E. coli* cell).

In a fourth aspect, the present invention contemplates a multicellular structure comprising one or more cells of the third aspect of the invention.

In one embodiment, the multicellular structure comprises a plant or a part, organ or tissue thereof. As referred to herein, "a plant or a part, organ or tissue thereof" should be understood to specifically include a whole plant; a plant tissue; a plant organ; a plant part; a plant embryo; and cultured plant tissue such as a callus or suspension culture.

As would be appreciated from the remainder of the specification the plant or a part, organ or tissue thereof contemplated in the fourth aspect of the invention may include, for example, any of a monocot, cereal crop, wheat, rice or barley plant or part, organ or tissue thereof.

In some embodiments of the fourth aspect of the invention, the plant or part, organ or tissue thereof comprises a plant seed.

In some embodiments of the fourth aspect of the invention, a nucleotide sequence of interest may be operably connected to the transcriptional control sequence or the functionally active fragment or variant thereof, such that the nucleotide sequence of interest is specifically or preferentially expressed in a plant seed, or in a particular cell or tissue type thereof, and optionally at a particular developmental stage, as described above with respect to the first aspect of the invention.

In a fifth aspect, the present invention provides a method for specifically or preferentially expressing a nucleotide sequence of interest in a plant seed, the method comprising effecting transcription of the nucleotide sequence of interest in a plant under the transcriptional control of the nucleic acid of any one of the first aspect of the invention.

As set out above, in its fifth aspect, the present invention is predicated, in part, on effecting transcription of the nucleotide sequence of interest under the transcriptional control of a transcriptional control sequence of the first aspect of the invention. In one embodiment, this is effected by introducing a nucleic acid molecule comprising the transcriptional control sequence, or a functionally active fragment or variant thereof, into a cell of the plant, such that the nucleotide sequence of interest is operably connected to the transcriptional control sequence. The nucleic acid molecule may be introduced into the plant via any method known in the art. For example, an explant or cultured plant tissue may be transformed with a nucleic acid molecule, wherein the explant or cultured plant tissue is subsequently regenerated into a mature plant including the nucleic acid molecule; a nucleic acid may be directly transformed into a plant seed, either stably or transiently; a nucleic acid may be introduced into a seed via plant breeding using a parent plant that carries the nucleic acid molecule; and the like.

In one embodiment, the nucleic acid molecule is introduced into a plant cell via transformation. Plants may be transformed using any method known in the art that is appropriate for the particular plant species. Common methods include *Agrobacterium*-mediated transformation, microprojectile bombardment based transformation methods and direct DNA uptake based methods. Roa-Rodriguez et al. (*Agrobacterium-mediated transformation of plants*, 3$^{rd}$ Ed. CAMBIA Intellectual Property Resource, Canberra, Australia, 2003) review a wide array of suitable *Agrobacterium*-mediated plant transformation methods for a wide range of plant species. Other bacterial-mediated plant transformation methods may also be utilised, for example, see Broothaerts et al. (2005, supra). Microprojectile bombardment may also be used to transform plant tissue and methods for the transformation of plants, particularly cereal plants, reviewed by Casas et al. (*Plant Breeding Rev.* 13: 235-264, 1995). Direct DNA uptake transformation protocols such as protoplast transformation and electroporation are described in detail in Galbraith et al. (eds.), *Methods in Cell Biology* Vol. 50, Academic Press, San Diego, 1995). In addition to the methods mentioned above, a range of other transformation protocols may also be used. These include infiltration, electroporation of cells and tissues, electroporation of embryos, microinjection, pollen-tube pathway-, silicon carbide- and liposome mediated transformation. Methods such as these are reviewed by Rakoczy-Trojanowska (*Cell. Mol. Biol. Lett.* 7: 849-858, 2002). A range of other plant transformation methods may also be evident to those of skill in the art and, accordingly, the present invention should not be considered in any way limited to the particular plant transformation methods exemplified above.

As set out above, the transcriptional control sequence of the present invention is introduced into a plant cell such that the nucleotide sequence of interest is operably connected to the transcriptional control sequence and the present invention contemplates any method to effect this. For example, the subject transcriptional control sequence and a nucleotide sequence of interest may be incorporated into a nucleic acid molecule such that they are operably connected, and this construct may be introduced into the target cell. In another example, the nucleic acid sequence of the present invention may be inserted into the genome of a target cell such that it is placed in operable connection with an endogenous nucleic acid sequence. As would be recognised by one of skill in the art, the insertion of the transcriptional control sequence into the genome of a target cell may be either by non-site specific insertion using standard transformation vectors and protocols or by site-specific insertion, for example, as described in Terada et al. (*Nat Biotechnol* 20: 1030-1034, 2002).

The nucleotide sequence of interest, which is placed under the regulatory control of the transcriptional control sequence of the present invention, may be any nucleotide sequence of interest. General categories of nucleotide sequences of interest include nucleotide sequences which encode, for example: reporter proteins, such as, GUS, GFP and the like; proteins involved in cellular metabolism such as Zinc finger proteins, kinases, heat shock proteins and the like; proteins involved in agronomic traits such as disease or pest resistance or herbicide resistance; proteins involved in grain characteristics such as grain biomass, nutritional value, post-harvest characteristics and the like; heterologous proteins, such as proteins encoding heterologous enzymes or structural proteins or proteins involved in biosynthetic pathways for heterologous products; "terminator" associated proteins such as barnase, barstar or diphtheria toxin. Furthermore, the nucleotide sequence of interest may alternatively encode a non-translated RNA, for example an siRNA, miRNA, antisense RNA and the like.

The method of the present invention may be applicable to effect specific or preferential expression of a nucleotide sequence of interest in a range of different plant seeds. For example, in one embodiment, the plant seed may be a monocotyledonous plant seed. In another embodiment, the plant seed may be a cereal crop plant seed.

In one specific embodiment, the method of the present invention may be applicable to effect specific or preferential expression of a nucleotide sequence of interest in a wheat seed.

In a further specific embodiment, the method may be applicable to effect specific or preferential expression of a nucleotide sequence of interest in one or more wheat seed tissues selected from the list consisting of: the endosperm transfer layer, the starchy endosperm and the aleurone tissue.

In a yet further specific embodiment, the method may be applicable to effect specific or preferential expression of a nucleotide sequence of interest in a wheat seed, or one or more cell or tissue types therein, at least between 4 DAP and 13 DAP.

In another specific embodiment, the method of the present invention may be applicable to effect specific or preferential expression of a nucleotide sequence of interest in a barley seed.

In a further specific embodiment, the method may be applicable to effect specific or preferential expression of a nucleotide sequence of interest in one or more barley seed tissues selected from the list consisting of: the endosperm transfer layer and the starchy endosperm.

In a yet further specific embodiment, the method may be applicable to effect specific or preferential expression of a nucleotide sequence of interest in a barley seed, or one or more cell or tissue types therein, at least between 11 DAP and 34 DAP.

In yet another specific embodiment, the method of the present invention may be applicable to effect specific or preferential expression of a nucleotide sequence of interest in a rice seed.

In a further specific embodiment, the method may be applicable to effect specific or preferential expression of a nucleotide sequence of interest in one or more rice seed tissues selected from the list consisting of: the starchy endosperm and the embryo surrounding region.

In a yet further specific embodiment, the method may be applicable to effect specific or preferential expression of a nucleotide sequence of interest in a rice seed, or one or more cell or tissue types therein, at least between 8 DAP and 47 DAP.

In further embodiments, the transcriptional control sequences of the present invention may also specifically or preferentially direct the expression of an operably connected nucleotide sequence in a dicotyledonous plant, or a seed, tissue or cell thereof.

In further embodiments of the method of the fifth aspect of the invention, the nucleotide sequence of interest is heterologous with respect to the transcriptional control sequence, as defined supra.

Finally, reference is made to standard textbooks of molecular biology that contain methods for carrying out basic techniques encompassed by the present invention, including DNA restriction and ligation for the generation of the various genetic constructs described herein. See, for example, Maniatis et al., *Molecular Cloning: A Laboratory Manual* (Cold Spring Harbor Laboratory Press, New York, 1982) and Sambrook et al. (2000, supra).

The present invention is further described by the following non-limiting examples:

EXAMPLE 1

Figure 1:
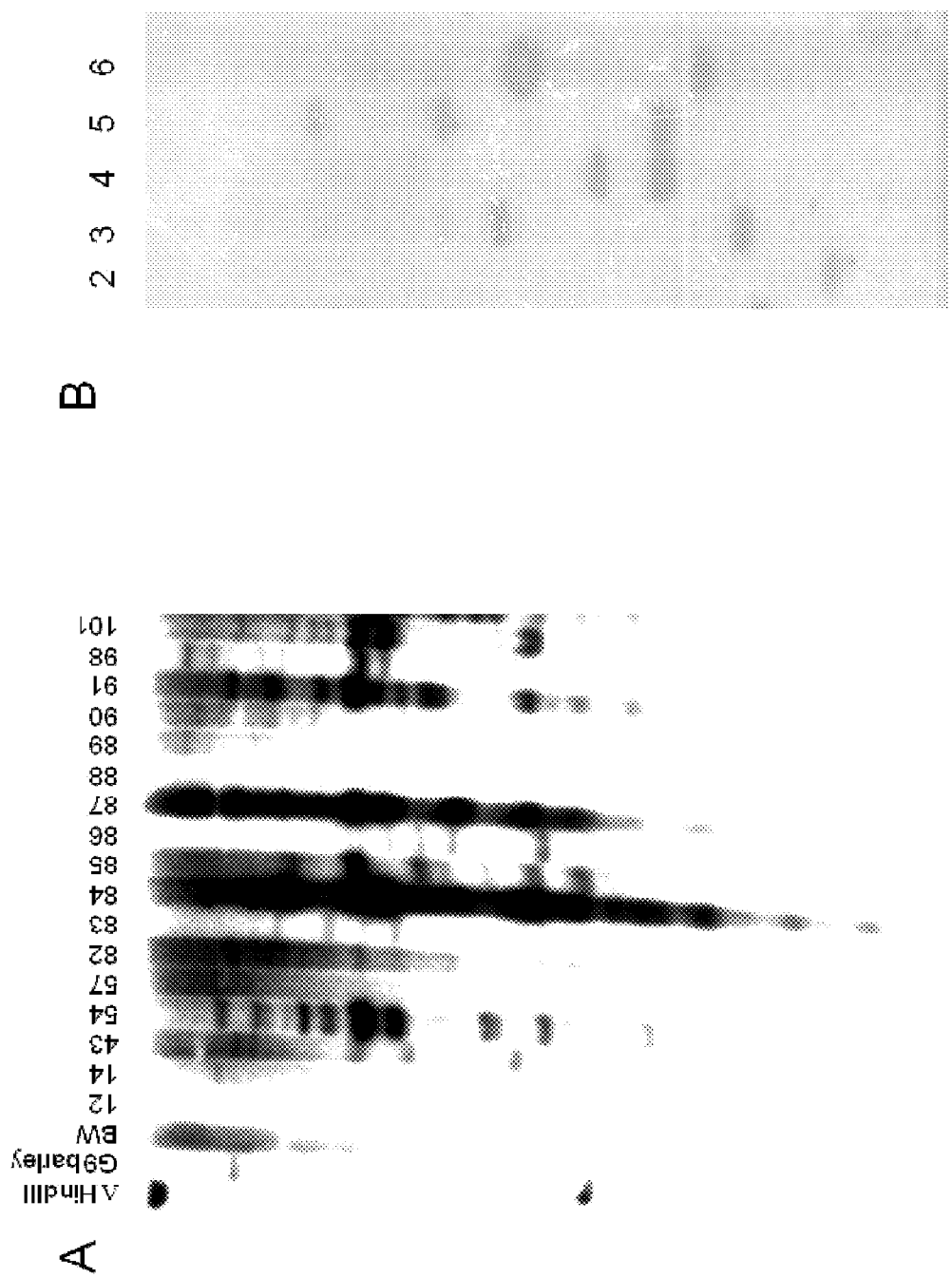
FIG. 1 shows a Southern Blot confirming the successful integration of pMDC164-TdPR60 into transgenic wheat (A) and barley (B) plant lines. Either part of the coding region of GUS (A) or the whole coding region of Hygromycin phosphotransferase (B) were used as probes. A. Wheat transgenic lines: λ HindIII—molecular size marker, λ DNA cut with HindIII; 9G—positive control, 9G transgenic line of barley with two copies of GUS transgene; BW—negative control wild type wheat cv. BobWhite; numbers over the rest of lanes correspond to independent transgenic lines; B. Barley transgenic lines: 2—line G86-2, 3—line G86-3, 4—line G86-4, 5—line G86-5, 6—line G86-6. The number of bands reflects the number of integrated copies of the vector.
Figure 2:
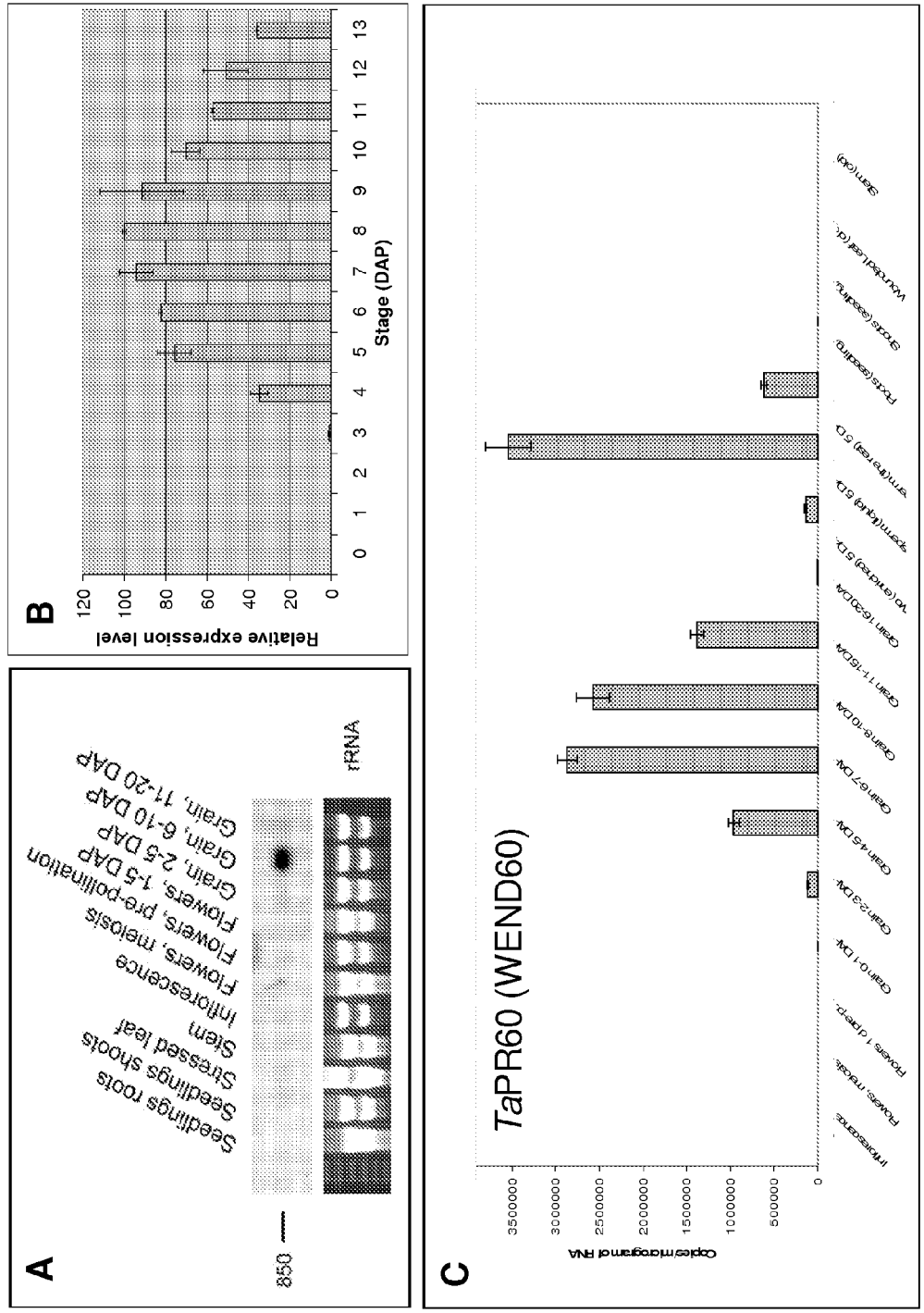
FIG. 2 shows levels of expression of TaPR60 in different wheat tissues (A), in grain at different stages of development (B) and in grain fractions at 5 DAP (C) studied by northern blot hybridization (A) and quantitative RT-PCR (B and C)

Isolation of Promoter Sequences and Preparation of Reporter Constructs

The cDNA of TaPR60 was isolated from the cDNA library prepared from the liquid part of the syncytial endosperm of *Triticum aestivum* at 3-6 DAP. A single cDNA of TaPR60 was identified among about 200 cDNAs randomly selected for sequencing.

The full length cDNA sequence of TaPR60 was used to probe BAC libraries prepared from genomic DNA of *Triticum durum* cv. Langdon (described in Cenci et al., *Theor Appl Genet* 107: 931-939, 2003) using Southern hybridisation as described in Example 2. Seven BAC clones which strongly hybridised with the probe were selected for further analysis. The *T. durum* homolog of TaPR60 (putatively contained within the BACs) was designated TdPR60.

EXAMPLE 2

Hybridisation Protocol for BAC Colony Membranes

Pre-Hybridisation Procedure

Membranes were soaked in 5×SSC making sure that any residual precipitated SDS on pre-used filters had re-dissolved. The membranes were then placed into a bottle and approximately 30 ml of pre-hybridisation solution (see below) was added before incubating overnight at 65° C.
Pre-Hybridisation Solution 300 ml of pre-hybridisation solution was prepared by mixing: 150 ml 10×SSC, 105 ml nanopure water, 30 ml Denhardt's III and 15 ml salmon sperm DNA (5 mg/ml, autoclaved) followed by incubation at 55-65° C. for 5 minutes.
Hybridisation Procedure After pre-hybridisation, the pre-hybridisation solution in the bottle was replaced with hybridisation solution prior to adding the labelled probe.

500 µl carrier DNA (5 mg/ml, autoclaved) was added to the labelled probe. This was boiled for 5 minutes, then chilled for a further 5 minutes on ice, and then added to the bottle. The bottle was then incubated overnight at 65° C. The hybridisation mix was then poured out, leaving the membrane in the bottle. The membrane was washed with about 40-50 ml 2×SSC, 0.1% SDS before further incubation at 65° C. for about 20 minutes. The membrane was then removed from the bottle and transferred to storage container. The membranes were then washed with pre-warmed 1×SSC, 0.1% SDS at 65° C. using a shaking water bath for approximately 30 minutes. This wash step was repeated where needed. Finally, binding of the probe to the samples was then detected using standard autoradiography methods.
Hybridisation Solution 100 ml of Hybridisation Solution was prepared by mixing: 5 ml nanopure water, 30 ml 5×HSB buffer, 30 ml Denhardt's III, 30 ml 25% Dextran sulphate and 5 ml salmon sperm DNA (5 mg/ml, autoclaved) followed by incubation at 55-65° C. for 5 minutes.

EXAMPLE 3

DNA Isolation from BACs

DNA was isolated from positive clones selected according to the hybridisation technique (described above) using the method set out below:

7.5 ml of Luria Broth (LB) supplemented with chloramphenicol (Cm) was inoculated with a single colony before incubation overnight at 37° C. with shaking at 225 rpm. The cells were then resuspended in 400 µl P1 (QIAGEN #19051—Tris.Cl-EDTA resuspension buffer) buffer by vortexing. 400 µl P2 (QIAGEN #19052—NaOH/SDS lyses buffer) buffer was then added followed by gentle mixing and incubation at room temperature for no more than 5 min. 400 µl of P3 (QIAGEN #19053—acidic potassium acetate) was then added followed by gentle mixing and incubation on ice for 5 min. The samples were then centrifuged at 15000 rpm for 15 min at room temperature and the supernatant subsequently transferred to a new tube. 0.6 ml of 100% isopropanol was then added to the new tube. The samples were then mixed followed by centrifugation at 15000 rpm for 15 min at room temperature. Immediately after centrifugation, the supernatant was decanted without disturbing the pellet. The DNA pellet was then washed by adding 1 ml of room-temperature 70% ethanol followed by centrifugation and decanting of the supernatant as described above. The pellet was then air-dried before being resuspended in 500 µl TE+5 µl RNAase cocktail (Geneworks, cat #AM-2286) followed by incubation at 37° C. for 15 min. 500 µl of (25:24:1) phenol: chloroform: isoamyl alcohol was then added followed by centrifugation at 15000 rpm for 10 min at room temperature. After centrifugation, the aqueous phase was removed and transferred to a new tube, to which 50 µl 3M Sodium Acetate pH 5.2 and 300 µl 100% isopropanol were added before incubation at −20° C. for 60 min. After incubation, the sample was centrifuged at 15000 rpm for 15 min at room temperature and the supernatant removed. The resulting DNA pellet was then washed with 1 ml of 70% ethanol followed by centrifugation at 15000 rpm for 5 min and removal of the supernatant. The final pellet was then air-dried before being resuspended in 30 µl TE pH 8.

EXAMPLE 4

Amplification and Cloning of TdPR60 Sequences from BAC DNA

The TdPR60 promoter sequence was first identified on the BAC clone by several consecutive sequencing reactions. In the first sequencing reaction, reverse primers derived from the 5' end of the gene sequence were used. In subsequent PCR reactions, primers were used that were derived from segments of DNA obtained during sequencing. As a result of such 'walking' along the DNA, about 3000 bp of sequence upstream from the TdPR60 translation start codon was obtained. This sequence was subsequently used to design forward and reverse primers for the isolation of the promoter segment.

A promoter with a full-length 5'-untranslated region of TdPR60 was isolated by PCR using AccuPrime™ Pfx DNA polymerase (Invitrogen) from DNA of BAC clone W60-1 as a template using the primers shown below in Table 2. The length of promoter used in constructs was 2147 bp.

TABLE 2

Primers used to amplify the 5'-untranslated region (promoter) of TdPR60

| Primer | Sequence | Sequence ID |
|---|---|---|
| BACW60R1 | 5'-ttgcatgcagggttgctagctag-3' | SEQ ID NO: 5 |
| BACW60R2 | 5'-gaagatatagcaccgtgtcagac-3' | SEQ ID NO: 6 |
| BACW60R3 | 5'-ggaaaagtaacagggctgtgaag-3' | SEQ ID NO: 7 |
| BACW60R4 | 5'-acaattgatatacagagctttgg-3' | SEQ ID NO: 8 |
| BACW60R5 | 5'-agaagttgctgggatacggtgtc-3' | SEQ ID NO: 9 |
| BACW60R6 | 5'-atcgagcagttccacgacgtgac-3' | SEQ ID NO: 10 |
| BACW60R7 | 5'-cactgggcgacacggcacttgtc-3' | SEQ ID NO: 11 |
| BACW60R8 | 5'-gacgacgatggcgttcgacgaag-3' | SEQ ID NO: 12 |
| pBACW60R9 | 5'-ctacaaagccatgaccacgagtg-3' | SEQ ID NO: 13 |
| pBACW60R10 | 5'-ggtgctccttcttcttctatctc-3' | SEQ ID NO: 14 |
| C-BACW60a | 5'-caccagaagaagaaggagcaccaatac-3' | SEQ ID NO: 15 |

As shown in table 2, the tetranucleotide sequence CACC was introduced into the 5' ends of the forward primer (C-BACW60). The PCR product including the TdPR60 promoter sequence was directionally cloned into the pENTR-D-TOPO vector using pENTR Directional TOPO Cloning Kits (Invitrogen). The construct was linearised with MluI and used for cloning of the promoter by recombination into the destination binary vector for plant transformation, pMDC164 (Curtis and Grossniklaus, *Plant Physiol.* 133: 462-469, 2003), upstream of a β-glucoronidase (GUS) cDNA.

This construct was subsequently used for barley transformation, as described in the following example and may also be used for transformation of other cereals such as rice and wheat.

EXAMPLE 5

Plant transformation

Barley Transformation

*Agrobacterium tumefaciens*-mediated transformation of barley (*Hordeum vulgare* cv Golden Promise) was performed with plasmid pMDC164-TdPR60 promoter using the procedure developed by Tingay et al. (*Plant J.* 11: 1369-1376, 1997) and modified by Matthews et al. (*Mol Breed.* 7: 195-202, 2001). Developing spikes were harvested from donor plants grown in the glasshouse when the immature embryos were approximately 1-2 mm in diameter. The immature embryos were aseptically excised from the surface-sterilised grain, and the scutella were isolated by removing the embryonic axes. Twenty five freshly isolated scutella were cultured cut side-up in the centre of a 90 mm×10 mm Petri dish containing callus induction medium, based on the recipe of Wan and Lemaux (*Plant Physiol.* 104: 37-48, 1994). This medium is composed of MS macro-nutrients (Murashige and Skoog, *Physiol. Plant.* 15: 473-497, 1962), FHG micro-nutrients (Hunter, *Plant regeneration from microspores of barley, Hordeum vulgare*, PhD thesis, Wye College, University of London, Ashford, Kent, 1988), supplemented with 30 g/L maltose, 1 mg/L thiamine-HCl, 0.25 g/L myo-inositol, 1 g/L casein hydrolysate, 0.69 g/L L proline, 10 μM $CuSO_4$, 2.5 mg/L Dicamba (3,6-dichloro-o-anisic add), and is solidified with 3.5 g/L Phytagel (Sigma Chemicals, St. Louis, Mo., USA). *Agrobacterium* suspension (50 ml) was aliquotted onto the scutella, and the Petri dish was held at a 45° angle to drain away excess bacterial suspension. The explants were then turned over and dragged across the surface of the medium to the edge of the Petri dish. The scutella were transferred to a fresh plate of callus induction medium and cultured cut side-up for three days in the dark at 22-24° C.

Following co-cultivation, the scutella were removed to fresh callus induction medium containing 95 μM hygromycin B (Becton Dickinson Biosciences, Palo Alto, Calif., USA) and cultured in the dark. The entire callus of an individual scutellum was transferred to fresh selection medium every fortnight for a further six weeks. At the end of the callus selection period, the callus derived from each treated scutellum was transferred to shoot regeneration medium. This medium is based on the FHG recipe of Wan and Lemaux (1994, supra). It contains FHG macro- and micro-nutrients (Hunter, 1988, supra), 1 mg/L thiamine-HCl, 1 mg/L benzylaminopurine (BAP), 0.25 g/L myo-inositol, 0.73 g/L L-glutamine, 62 g/L maltose, 10 μM $CuSO_4$, 38 μM hygromycin B, and is solidified with 3.5 g/L Phytagel. The cultures were exposed to light (16 h day/8 h night photo-period) for three to four weeks at 22-24° C. The regenerated shoots were excised from the callus and transferred to culture boxes (Magenta Corporation, Chicago, Ill., USA) that contained hormone-free callus induction medium, supplemented with 95 μM hygromycin B to induce root formation. The tissue culture-derived plants were finally established in soil and grown to maturity.

All the above media contain 150 mg/L Timentin (Smith-Kline Beecham, Pty. Ltd., Melbourne, Australia) to inhibit the growth of *Agrobacterium tumefaciens* following co-cultivation.

Rice Transformation

Seed embryo-derived callus of cv. Nipponbare (*Oryza sativa* ssp. *japonica*) is co-cultured with the *Agrobacterium* strain EHA105 or LBA4404 carrying the pMDC164-TdPR60 promoter plasmid following the procedure detailed in Sallaud et al. (*Theor. Appl. Genet.* 106: 1396-1408, 2003).

Dehulled seeds are sterilised, inoculated on NB medium and incubated for 18-21 days in the dark as described in Chen et al. (*Plant Cell Rep.* 18: 25-31, 1998). Embryogenic nodular units (0.5-1 mm long), released from the primary embryo scutellum-derived callus at the explant/medium interface, are transferred onto fresh NB medium and incubated for an additional 10-15 days depending on the variety.

Between 50 and 100, 3- to 5-mm-long, embryogenic nodular units are immersed into 25 ml of liquid co-culture medium (CCL) containing *Agrobacterium* cells at a density of 3-5× $10^9$ cells ml$^{-1}$ ($OD_{600}$=1) in a 100 mm diameter petri dish for 10-15 min. Ten callus pieces are then blotted dry on sterilised filter paper, transferred to a petri dish containing solid co-culture medium (CCS) and incubated for 3 days at 25° C. in the dark. Five to seven uncontaminated co-cultured calli are then individually transferred to one dish of R2S (Ohira et al., *Plant & Cell Physiol.* 14: 1113-1121, 1973) selection medium, which contains hygromycin for selection of transformed tissues and cefotaxime and vancomycin for eliminating *Agrobacterium*, and incubated at 27° C. in the dark.

Following 2 weeks of selection on R2S medium, the calli are transferred to NBS medium. After 1 week of incubation, the protuberances develop into brownish globular structures, which are gently teased apart with forceps on the medium around the original callus and incubated for 10-15 days in the resealed petri dish. After co-culture, the globular structures evolve into calli.

The putatively transgenic, hygromycin-resistant calli are gently picked out, placed on the PRAG pre-regeneration medium and incubated for a further week. All of the resistant calli originating from a single co-cultured embryogenic nodular unit are grouped in a sector of the PRAG dish, which can accommodate 40-50 resistant calli.

Four to five, creamy-white, lobed calli with a smooth and dry appearance are individually transferred to one dish of RN regeneration medium, kept for 2 days in the dark, then maintained for 3 weeks under a 12/12-h (day/night) photoperiod. Shoots regenerating from a resistant callus are dissected and sub-cultured in test tubes containing P medium for a further 3-week growth period to promote vigorous tiller and root development before being transferred to Jiffy peat pellets in the containment greenhouse for acclimatisation.

Wheat Transformation

Immature seeds of wheat cv. Bobwhite were surface-sterilized by immersing into 70% ethanol for 2 min, followed by incubation in 1% sodium hypochlorite solution with shaking at 125 rpm for 20 min and finally by three washes in sterile distilled water. Immature embryos (1.0-1.5 mm in length, semitransparent) were isolated aseptically and were placed, with the scutellum side up, on solid culture medium. Embryos developing compact nodular calli were selected using a stereomicroscope and used for bombardment 7-21 days after isolation. The cultures were kept in the dark at 25° C. on solid MS (Duchefa, M0222; Murashige and Skoog 1962) with 30 g/l sucrose, 2 mg/l 2,4-D (MS2).

Plasmid constructs were purified using Macherey-Nagel or Qiagen kits according to the manufacturers protocols.

A DNA-gold coating according to the protocol of Sanford et al. (In: *Methods in Enzymology*, ed. R. Wu, 217: 483-509, 1993) was performed as follows: 50 µl of gold powder (1.0 µm) in 50% glycerol (60 mg/ml) was mixed with 10 µl DNA (1 mg/ml), 50 µl $CaCl_2$ (2.5M) and 20 µl of 0.1 M spermidine. For co-transformation the plasmids were mixed at a ratio 1:1 (5 µg+5 µg). The mixture was vortexed for 2 min, followed by incubation for 30 min at room temperature, brief centrifugation, and serial washing in 70% and 99.5% ethanol. Finally, the pellet was resuspended in 60 µl of 99.5% ethanol (6 µl/shot). All manipulations were done at room temperature.

Microprojectile bombardment was performed utilizing the Biolistic PDS-1000/He Particle Delivery System (Bio-Rad). Before bombardment, immature embryos were pre-treated for 4 hours on MS2 medium supplemented with 100 g/l sucrose. Embryos (50/plate) were then placed in the centre of a plate to form a circle with a diameter of 10 mm. Bombardment conditions were 900 or 1100 psi, with a 15 mm distance from the macrocarrier launch point to the stopping screen and a 60 mm distance from the stopping screen to a target tissue. The distance between the rupture disk and the launch point of the macrocarrier was 12 mm. 16 hours after bombardment, the calli were transferred to MS2 medium and grown in dark for one week.

Two days after bombardment the treated calli were transferred to MS selection medium supplemented with 2.0 mg/l 2,4-D and 150 mg/l hygromycin B. After 3-6 selections (4-6 months) greening callus tissues were subcultured on MS regeneration medium supplemented with 1 mg/l kinetin and 5-10 mg/l zeatin. Regenerating plantlets were then transferred to jars with the half-strength hormone-free MS medium supplemented with 50 mg/l hygromycin B.

The fully developed plantlets were acclimated for 7-10 days at room temperature in a liquid medium containing four-fold diluted MS salts. Plants with strong roots were then transplanted into soil and grown under greenhouse conditions to maturity.

EXAMPLE 6

Detection of the Selectable Marker in Transformants

The presence of the transformation vector in the putative transformed plants was investigated by using Southern blotting to detect either the GUS-encoding gene (in wheat) or the hpt selectable marker (in barley) in DNA isolated from putatively transformed plant tissue.

FIG. 1 shows a Southern Blot confirming the successful integration of pMDC164-TdPR60 into transgenic wheat and barley plant lines. In this figure, the number of bands hybridising with the probe reflects the number of integrated copies of the vector.

Plant DNA Isolation

Leaf samples were homogenised in Eppendorf tubes with a sand powder in 0.3-5.0 ml of hot (55° C.) 2×CTAB solution. Equal volume of the CTAB solution and 0.6-10.0 ml of chloroform-isoamyl alcohol mixture (24:1 v/v) were added to the extracts. The tubes were incubated on a shaker (Mild Mixer PR-12, TAITEC) at speed 5 at room temperature for 15-30 min. Phases were separated by centrifugation (3600-15000 rpm, 20° C., 5 min) and the supernatants were carefully transferred into new tubes with 0.6-10.0 ml isopropanol. DNA pellets (12 000-15 000 rpm, 20° C., 20 min) were washed with 70% ethanol, resuspended in 0.3-1.0 ml TE and RNAse treated for 30 min. After two sequential chloroform extractions DNA samples were pelleted by adding 0.1-0.33 ml of 10 M $NH_4Ac$ and 0.3-1.0 ml of isopropanol (15 000 rpm, 20° C., 20 min). Pellets were sequentially washed with 70% and 99.5% ethanol and then redissolved in 20-500 ml of 0.1 TE.

Southern Blotting

Isolated plant DNA was digested with XhoI enzyme and subjected to agarose gel electrophoresis and staining with ethidium bromide.

A Southern transfer assembly was constructed as follows: a sponge soaked in 0.4 M NaOH was placed in a Perspex tray. One sheet of filter paper soaked in 0.4 M NaOH was then placed over the sponge. The agarose gel was then overlaid on the soaked filter paper. A Hybond N+ membrane was then serially soaked in nanopure water and in 0.4 M NaOH for 30 seconds before being overlaid on the agarose gel. A further sheet of filter paper soaked in 0.4 M NaOH was then placed on top of the membrane, followed by a 10 cm stack of dry paper towels. A glass plate was then placed on top of the stack and the perspex tray was filled with 0.4 M NaOH.

The DNA was then allowed to transfer for at least 2 hours before disassembly of the transfer assembly. The membrane was then rinsed for 1 minute in 100 ml 2×SSC and blotted dry on filter paper.

The membrane was then probed either with 0.7 kb fragment of the coding region of GUS cDNA or with a 1.1 kb fragment of the hygromycin phosphotransferase gene (hpt) amplified from the vector pCAMBIA1380 using standard techniques.

EXAMPLE 7

β-glucuronidase Assays

β-glucuronidase activity in transgenic plants was analysed by histochemical staining using the chromogenic substrate 5-bromo-4-chloro-3-indolyl-β-glucuronic acid (X-Gluc) (Bio Vectra) as described by Hull and Devic (*Methods Mol Biol.* 49: 125-141, 1995).

Different plant organs, whole grain and grain sections of different ages were immersed in a 1 mg/ml X-Gluc solution in 50 mM sodium phosphate, pH 7.0, 10 mM Na EDTA, 2 mM $FeK_3(CN)_6$, 2 mM $K_4Fe(CN)_6$ and 0.1% Triton X-100. After vacuum infiltration at ~75 KPa for 20 min, the samples were incubated at 37° C. until satisfactory staining was observed. Tissues were then serially incubated in 20%, 35% and 50% ethanol before being fixed in FAA (50% ethanol, 10% glacial acetic acid, 5% formaldehyde) and cleared in 70% ethanol. Pictures were taken using a LEICA MZFLIII microscope and a LEICA P/N:10446271 camera.

For wax embedding, grain sections were serially dehydrated in 80%, 95%, and 100% ethanol. The samples were then serially incubated in 25% xylene in molecular sieve 100% ethanol (1:3) for 1 hour; 50% xylene: 50% molecular sieve 100% ethanol (1:1) for 1 hour; and 100% xylene for 1 hour. The samples were then incubated in paraffin wax for at least 6 hours at 60° C. This step was repeated such that the wax was changed at least six times before embedding.

The sectioning and mounting was carried out on a Leica RM2265 microtome. Each individual grain segment was cut into 12 μm-thick sections and the ribbons were mounted onto saline-coated slides. The slides were dried on a 42° C. slide warmer overnight and deparaffinized.

For counter staining, the slides were soaked in xylene for 10 min and moved to fresh xylene for another 10 min or until the specimens were clear. The specimen on each slide was mounted in DPX medium and covered with a cover slip. The slides were air-dried in the fume hood overnight. The specimens were then observed on a compound microscope under bright-field illumination.

EXAMPLE 8

Transgene Insertion in Plants

The number of inserts in transgenic lines of barley varied from one (Line 2) to two (Line 3) and three (Lines 4-6). In wheat, the number of inserts varied from two to about 16 or more. The number of inserts in transgenic rice plants was not examined.

Six $T_0$ wheat lines were selected using the GUS staining assay, from which three were selected for further analysis. Ten $T_1$ progeny for each of the three lines were analysed. Among the 30 progeny there were two plants with very strong, two plants with relatively strong, and 13 plants with weak transgene expression; and 13 plants exhibited no GUS expression. All positive lines demonstrated the same pattern of GUS expression.

Eighteen $T_0$ barley lines were selected, from which two were used for the analysis of $T_1$ plants. From nine $T_1$ plants, one had strong, two plants had weak and six plants had no transgene expression. All $T_0$ and $T_1$ plants demonstrated the same pattern of GUS expression. The differences in expression levels between different transgenic lines showed no correlation with the number of inserts.

24 $T_0$ lines of transgenic rice were analysed for GUS activity. Eight lines demonstrated strong promoter activity and the same pattern of gene expression. The $T_1$ generation was analysed for two lines (six plants for each). All positive plants had the same patterns of transgene expression as $T_0$ plants. Wild type plants and/or plants transformed with a vector containing only the selectable marker cassette were used as negative controls. No differences were found between wild type plants and plants transformed with the control vector. The strength of the TdPR60 promoter in barley and rice remained the same in the $T_0$ and $T_1$ generations. In contrast, promoter strength in wheat significantly decreased in the $T_1$ generation relative to the corresponding $T_0$ parents.

EXAMPLE 9

Expression Pattern of the TdPR60 Promoter in Wheat

The expression pattern of the TdPR60 promoter was observed in wheat cv. Bobwhite transformed with GUS under the control of the TdPR60 promoter. GUS expression was detected using the method described in Example 7.

Figure 3A:
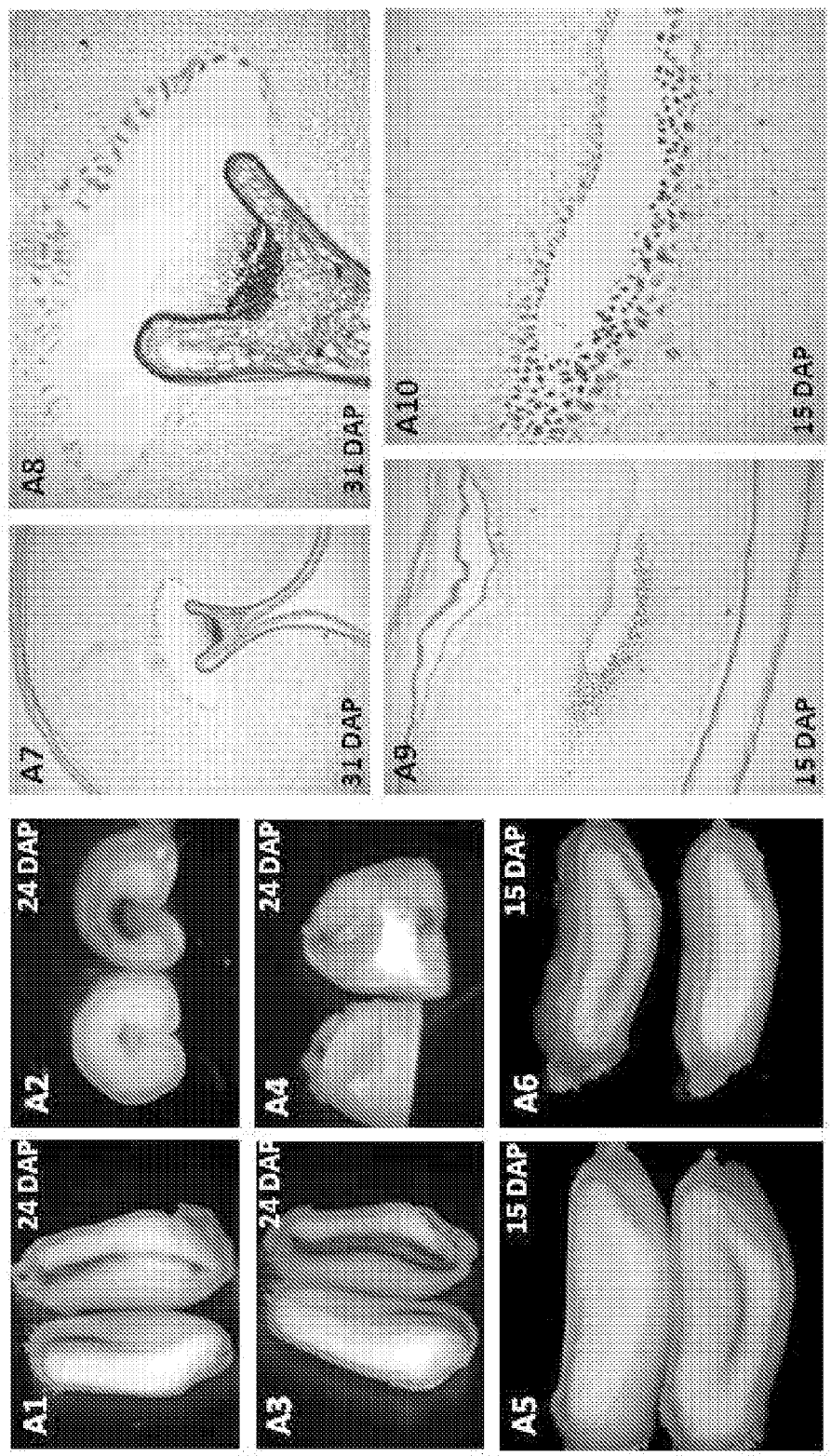
FIG. 3 shows the spatial and temporal GUS expression in wheat (FIG. 3A) and barley (FIG. 3B) directed by the TdPR60 promoter. GUS activity in wheat (A) and barley (B) was detected in hand-cut longitudinal (A1, A3, A5, A6, B1, B3-B7) and transverse sections (A2, A4, and B2) of transgenic lines, but no GUS activity was seen in wild type caryopses (presented on the same panels) at 9 DAP (B1), 13 DAP (B3, B6), 15 DAP (A5, A6, B4), 17 DAP (B7), 24 DAP (A1-A4), and 34 DAP (B2, B5). Grain from $T_0$ transgenic lines is shown in panels A1-A4 and B1-B5, while $T_1$ progeny are shown in panels A5, A6, B6 and B7. Histochemical GUS assay counter stained with safranin in: 10 µm thick transverse section of transgenic wheat (A7, A8) and barley (B9) caryopsis, and longitudinal section of transgenic wheat (A9, A10) and barley caryopsis (A8) at 15 DAP (A9, A10), 16 (B8), 31 (A7, A8) and 34 DAP (B9).

FIG. 3A shows the expression of a GUS reporter under the control of the TdPR60 promoter in a transgenic wheat line. As shown in the figures, GUS expression in the grain of transgenic wheat at 15 DAP was observed predominantly in the endosperm transfer cells. Lower GUS expression can also be detected in the endosperm transfer layer, the starchy endosperm and in the aleurone layer. No detectable expression was observed in other tissues.

EXAMPLE 10

Expression Pattern of the TdPR60 Promoter in Barley

The expression pattern of the TdPR60 promoter was observed in barley transformed with GUS under the control of the TdPR60 promoter. GUS expression was detected using the method described in Example 7.

Figure 3B:
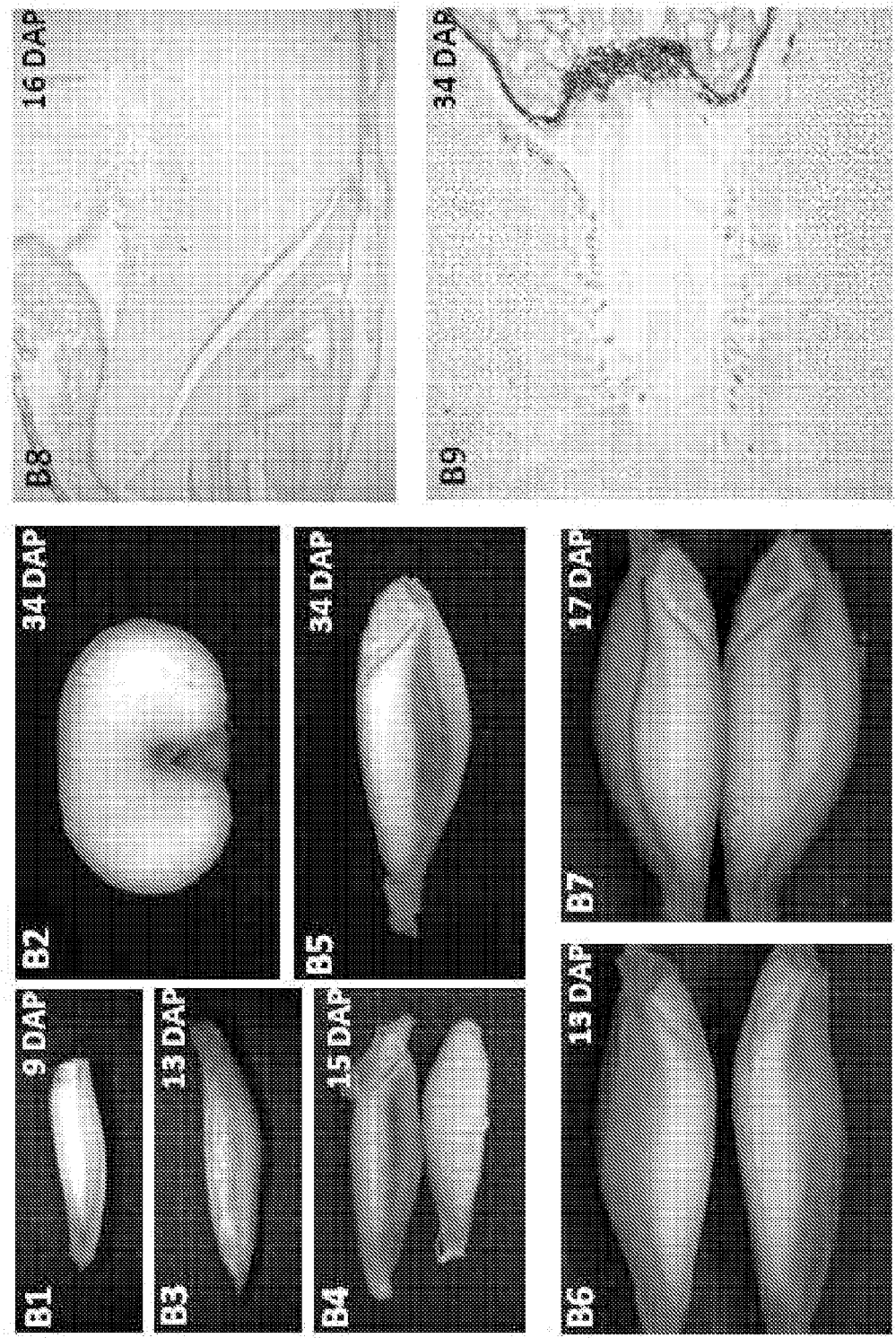

FIG. 3B shows the expression of a GUS reporter under the control of the TdPR60 promoter in a transgenic barley line. As shown in the figure, GUS staining was observed in the endosperm transfer cell layers and adjacent starchy endosperm.

EXAMPLE 11

Expression Pattern of the TdPR60 Promoter in Rice

The expression pattern of the TdPR60 promoter was observed in rice transformed with GUS under the control of the TdPR60 promoter. GUS expression was detected using the method described in Example 7.

Figure 4:
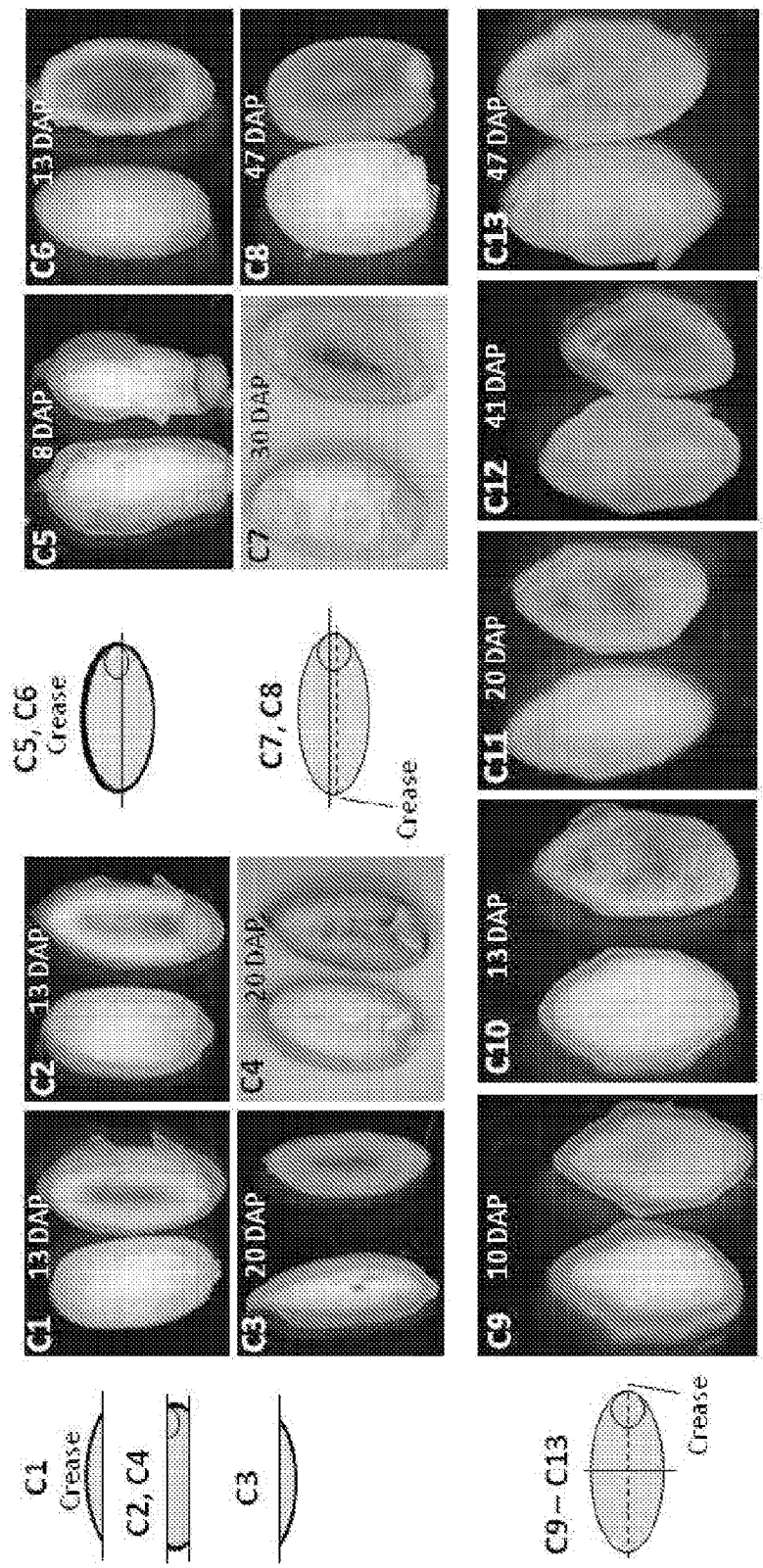
FIG. 4 shows the spatial and temporal GUS expression in rice directed by the TdPR60 promoter. GUS activity in rice is shown in hand-cut longitudinal (C1-C8) and transverse (C9-C13) sections of control (left side of each figure) and transgenic (right side of the figure) caryopses. GUS activity is detected in 8 DAP (C5), 10 DAP (C9), 13 DAP (C1, C2, C10), 20 DAP (C3, C11), 30 DAP (C7), 41 DAP (C12) and 47 DAP (C8, C13) old grain, but no GUS activity is seen in wild type caryopses (presented on the left side of same panels). A schematic representation of grain position during sectioning is also shown.

As shown in FIG. 4, GUS expression in the transgenic rice lines 6 and 10 was observed only in endosperm, predominantly in the starchy cells and embryo surrounding cells. GUS expression was observed at 8 DAP and continued to be observed at 47 DAP. At 8 DAP GUS expression was detected mainly in embryo surrounding region; no promoter activity was observed in embryo and aleurone transfer cells on all stages of development. Relatively strong GUS expression was found in the middle of the starchy endosperm and closer to the ventral side of the grain. Expression was strong starting from 13 DAP until 47 DAP. No detectable expression was observed in other tissues.

EXAMPLE 12

Sequence Analysis of the TdPR60 Promoter

Computer analysis of the TdPR60 promoter using PLACE software and a database of plant cis-acting regulatory DNA elements (Higo et al., *Nucleic Acids Research* 27(1): 297-300, 1999) revealed few cis-elements which are known to be involved in endosperm-specific activation. Among them is the RY repeat or legumin box, CATGCAC, found in seed storage protein genes (Fujiwara and Beachy, *Plant Molecular Biology* 24(2): 261-272, 1994). The RY repeats act together with the G box to provide seed specific, ABA-dependent gene expression (Ezcurra et al., *Plant Molecular Biology* 40(4): 699-709, 1999). However, the G-box motif was not present in the TdPR60 promoter. The promoter of TdPR60 did contain a $(CA)_n$ element, CCAAACAC, which was originally identified in storage proteins in *Brasica napus*, where it is responsible for both embryo and endosperm specific transcription (Ellerstrom et al., *Plant Molecular Biology* 32(6): 1019-1027, 1996). Several core sites for binding of Dof proteins (AAAG) were found to be concentrated in a 250 bp long region of the TdPR60 promoter. They can potentially provide interaction with PBF-like factors, which were demonstrated to bind to the prolamin box and specifically activate promoters in the endosperm (Diaz et al., *Plant Journal* 42(5): 652-662, 2005). However, a complete prolamin box was not identified. The (TATCTC) repeats, which specifically interact with ZmMRP-1 transcription factor and are responsible for ETC specific promoter activation in maize (Barrero et al., *Plant Molecular Biology* 62(4-5): 655-668, 2006), were not identified in the TdPR60 promoter.

EXAMPLE 13

Discussion

The spatial activities of the TdPR60 promoter in wheat and barley were nearly identical. In wheat and barley the promoter was active in endosperm transfer cells and adjacent layers of starchy endosperm. In barley, the spatial and temporal activity of the TdPR60 promoter was practically indistinguishable from the activity of the promoter of the rice gene OsPR602 (Li et al., *Plant Biotechnol J.* 6: 465-476, 2008). Surprisingly, in rice the TdPR60 promoter was activated early and was detected mainly inside of the starchy endosperm, in contrast to its activity in wheat and barley. Unlike the OsPR602 promoter in rice (Li et al., 2008, supra) no activity of the wheat promoter was identified in rice flowers or any other tissues. This suggests at least partial incompatibility of transcription factors and cis-elements responsible for ETC-specific activation of wheat and rice promoters. Use of strongly diverged or different cis-elements in rice and wheat is supported by the observation that identical or near-identical cis-elements in the TaPR60 and OsPR602 promoters could not be identified.

The expression pattern of TdPR60 suggests involvement of the gene product either in signal transduction or nutrient transfer into the endosperm. Although transcripts of TaPR60 were detected in endosperm as early as 3 DAP, at the beginning of coenocyte cellularisation, GUS activity was not observed before 9 DAP, when cellularisation of the endosperm was near completion. This result implies that the gene product is not involved in the endosperm cellularisation process. The difference between timing of mRNA and protein expression can be explained by possible translational regulation provided by the 5'UTR sequence, which was included in the promoter construct.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Also, it must be noted that, as used herein, the singular forms "a", "an" and "the" include plural aspects unless the context already dictates otherwise. Thus, for example, reference to "a nucleotide sequence of interest" includes a single nucleotide sequence as well as two or more nucleotide sequences; "a plant cell" includes a single cell as well as two or more cells; and so forth.

The claims defining the invention are as follows:

1. A nucleic acid construct comprising:
a transcriptional control sequence operably connected to a heterologous nucleotide sequence of interest, wherein the transcriptional control sequence specifically or preferentially directs expression of the operably connected heterologous nucleotide sequence of interest in a plant seed, and wherein said transcriptional control sequence comprises the nucleotide sequence set forth in SEQ ID NO: 3.

2. The nucleic acid construct of claim 1 wherein the transcriptional control sequence specifically or preferentially directs expression of an operably connected nucleotide sequence in a monocotyledonous plant seed.

3. The nucleic acid construct of claim 1 wherein the transcriptional control sequence specifically or preferentially directs expression of an operably connected nucleotide sequence in a cereal crop plant seed.

4. The nucleic acid construct of claim 3 wherein the transcriptional control sequence specifically or preferentially directs expression of an operably connected nucleotide sequence in a wheat seed.

5. The nucleic acid construct of claim 4 wherein the transcriptional control sequence specifically or preferentially directs expression of an operably connected nucleotide sequence in one or more plant seed tissues selected from the list consisting of: the endosperm transfer layer, the starchy endosperm and the aleurone tissue.

6. The nucleic acid construct of claim 4 wherein the transcriptional control sequence specifically or preferentially directs expression of an operably connected nucleotide sequence at least between 4 days after pollination (DAP) and 13 DAP.

7. The nucleic acid construct of claim 3 wherein the transcriptional control sequence specifically or preferentially directs expression of an operably connected nucleotide sequence in a barley seed.

8. The nucleic acid construct of claim 7 wherein the transcriptional control sequence specifically or preferentially directs expression of an operably connected nucleotide sequence in one or more plant seed tissues selected from the list consisting of: the endosperm transfer layer and the starchy endosperm.

9. The nucleic acid construct of claim 7 wherein the transcriptional control sequence specifically or preferentially directs expression of an operably connected nucleotide sequence at least between 11 DAP and 34 DAP.

10. The nucleic acid construct of claim 3 wherein the transcriptional control sequence specifically or preferentially directs expression of an operably connected nucleotide sequence in a rice seed.

11. The nucleic acid construct of claim 10 wherein the transcriptional control sequence specifically or preferentially directs expression of an operably connected nucleotide sequence in one or more plant seed tissues selected from the list consisting of: the starchy endosperm and the embryo surrounding region.

12. The nucleic acid construct of claim 10 wherein the transcriptional control sequence specifically or preferentially directs expression of an operably connected nucleotide sequence at least between 8 DAP and 47 DAP.

13. The nucleic acid construct of claim 1 wherein the transcriptional control sequence is derived from a gene which comprises an open reading frame comprising the nucleotide sequence set forth in SEQ ID NO: 2, said open reading frame encoding a polypeptide comprising the amino acid sequence set forth in SEQ ID NO: 1.

14. A cell comprising the nucleic acid construct of claim 1.

15. The cell of claim 14 wherein the cell is a plant cell.

16. A multicellular structure comprising one or more cells of claim 14.

17. The multicellular structure of claim 16 wherein the multicellular structure comprises a plant or a part, organ or tissue thereof.

18. A method for specifically or preferentially expressing a nucleotide sequence of interest in a plant seed, the method comprising introducing the nucleic acid construct of claim 1 into a plant.

19. The nucleic acid construct of claim 1, wherein said transcriptional control sequence consists of the nucleotide sequence set forth in SEQ ID NO: 3.

* * * * *

SEQUENCE LISTING

```
<160> NUMBER OF SEQ ID NOS: 15

<210> SEQ ID NO 1
<211> LENGTH: 102
<212> TYPE: PRT
<213> ORGANISM: Triticum durum
```

<400> SEQUENCE: 1

```
Met Ala Lys Leu Met Cys Leu Cys Phe Ile Ile Leu Ala Ile Ala Val
1               5                   10                  15

Ala Val Ser Ala Asp Glu Cys Glu Gly Asp Arg Gln Ala Met Ile Lys
            20                  25                  30

Glu Cys Ala Lys Tyr Gln Lys Trp Pro Ala Asn Pro Lys Leu Asp Pro
        35                  40                  45

Ser Asp Ala Cys Tyr Ala Val Trp Gln Lys Ala Asn Ile Pro Cys Leu
    50                  55                  60

Cys Ala Gly Val Thr Lys Glu Lys Glu Lys Ile Trp Ser Met Glu Lys
65                  70                  75                  80

Val Ala Tyr Val Ala Asn Phe Cys Lys Lys Pro Phe Pro His Gly Tyr
                85                  90                  95

Asn Tyr Thr Phe Pro Pro
            100
```

<210> SEQ ID NO 2
<211> LENGTH: 309
<212> TYPE: DNA
<213> ORGANISM: Triticum durum

<400> SEQUENCE: 2

| | |
|---|---:|
| atggcgaaac tcatgtgctt atgtttcatc atcctcgcta ttgcggtagc cgtgtcggct | 60 |
| gacgaatgtg agggtgaccg acaggccatg atcaaggagt gtgctaagta tcaaaaatgg | 120 |
| ccagcaaacc cgaagctaga tccgtcggac gcatgctacg ccgtgtggca gaaggcaaac | 180 |
| atcccatgcc tttgtgctgg tgtcaccaag gagaaagaga gatatggag tatggagaag | 240 |
| gttgcctacg ttgccaattt ctgcaagaag ccattcccac acggctacaa ttacacattc | 300 |
| cctccttga | 309 |

<210> SEQ ID NO 3
<211> LENGTH: 2147
<212> TYPE: DNA
<213> ORGANISM: Triticum durum

<400> SEQUENCE: 3

| | |
|---|---:|
| cactcgtggt catggctttg taggggcaca acaacgcagc gcccacgttt ccttgtgcgc | 60 |
| atgtacgcac gccgcctagc tagcaaccct gcatgcaatc ccatcagccc ggccatgcgc | 120 |
| actacatgcg cgctacgcac acgacgcggc catctccacc ggtcactgct aacaatcatc | 180 |
| taactaactc acacgcatca agcaaacttg gccggcacac ttgccaacgc cctgctctac | 240 |
| gtgccagact cgagagtata cacgctacac acacatgcgc cacgcttctg cgtcccgtac | 300 |
| gtcccgcccg tcccgcatgt catcgacgcg cccgtcaagc ccgacgagcc cgacggcacc | 360 |
| agtgtgtccc gcctgtccca cgcgcacccg acgcgcccga cgagcccgat cacacatgtc | 420 |
| gtggcttatt ccaaaacaca ccccttaagc cacggcctag aggagtccgt catcgtcgac | 480 |
| gttggcgccg gctaagagtg catgctccgc cgccggtcct ttccgcagct gcggcactc | 540 |
| gcgccggaag tgcccgtgct ccccgtactt gtagcagcgc ctgcgcctgt cgccgccgct | 600 |
| ccccgacgcc acgctgcgcc cgtcgtcgtc gtcccgagca ccgccgtgtc gacgctccca | 660 |
| tgctgcccac tgcgccaccg tcatgagcag ctgctcacct ccgcgctcgc cgccgtcttg | 720 |
| tccacagcgc cgaacccgct cgtcgaacgc acgcagccgc ccgagcgctt cgtcgaacgc | 780 |
| catcgtcgtc acgtcgtgga actgctcgat accggcgacg acggggaaga ggcgatccga | 840 |
| caccgtatcc cagcaacttc ttgacaagtg ccgtgtcgcc cagtgtctcc ccgaggttgg | 900 |

```
catacctcgc cgccatcgcc gcgagcctcc cgccgtacac gtcgagctcc tcgccgtcca    960
ccatcttcat ccggtcgaat ttgccatgca gcgtccccgg cctcgctgcg cgtacccgat   1020
cagcgcggac gaacctcacc ttcagggagt cccatacctc cctgacggtg agcttcgtcg   1080
ataccagcag cagcacatcc tccggcaacg ccccgagaag caacgtgcgc accatcttgt   1140
ccttccgcgc gttcaccacc gcgtcgcccg gcgccaccgc ctcccatacg gtgtggacgt   1200
cgaggatcgc ctacgccttg atgcccaga ccgtgtagtt gtccgcggtc agcaaaggca    1260
tcgccatcgt cgccgattcc gcccgcgccg ccgccgtgtg ggacgggcgc catggtcgcc   1320
ggtgatcgcc cgaaccaaag ctctgtatat caattgttgg aagcgctctc tcacactgat   1380
ggatggagat agaagaagaa ggagcacaca gtacaatgga gtttcacccg gcttcacagc   1440
cctgttactt ttcccagagc cccaaaaact ctcctcaaca aatacactcg tggtcatggc   1500
tttgtagtgg cacaacaaca caacgcccac gtttccttgt gcgcacgtat gcacaccgcc   1560
tagctagcta ccctgcatgc aatccatcag cccggccatg cgcactacat gcgcgctatg   1620
cgcatgacgc ggccatctcc accggtcact gctaacaatc agctaactaa ctcacacgca   1680
tcaagcaaac ttggccggca cacttgccaa cgccctgctc tatgtgctag actcgagtgt   1740
atacacgcta cacacacata tgccacgctt ctgcgtcccg catgtcccgc acgtcaccga   1800
cgcgcctgac aagcccgacg agccgacgg caccagtgtg tgccgcccgt tccgcgtgca    1860
cccgatgcgc tcgacgagcc cgatcacaca cgccgtggct tattccaaca cctagatgta   1920
taattaatgt atacattaat tgtctgacac ggtgctatat cttcatgata tacaactggt   1980
gtatgcgtct gtatcatcat ctcaaagaag gctatatata ccaagacata gctagcgaag   2040
tcatgtatcc cacacattca cagaagccac acaaatccta tattgtacga ttctaatatc   2100
aaagggatag agaaggctct agtgtaggag atacaaaagc catagcc                 2147

<210> SEQ ID NO 4
<211> LENGTH: 481
<212> TYPE: DNA
<213> ORGANISM: Triticum durum

<400> SEQUENCE: 4
atggcgaaac tcatgtgctt atgtttcatc atcctcgcta ttgcggtagc cgtgtcggct     60
gacgaatgtg agggtgaccg acaggccatg atcaaggagt gtgctaagta tcaaaaatgg    120
ccagcaaacc cgaagctaga tccgtcggac gcatgctacg ccgtgtggca gaaggcaaac    180
atcccatgcc tttgtgctgg tgtcaccaag gagaaagaga agatatggag tatggagaag    240
gttgcctacg ttgccaattt ctgcaagaag ccattcccac acggctacaa gtgcggaagt    300
aagtgaatat attaagggaa ttatgatgat cggcatttca tacatgcaat tttgatattt    360
attattcttt ggagtcacac gactttgatt ttagttatgc atttttatatg cttcttgcgc    420 tattctaatc atatgttggg tcaaattgaa tggtcttgca agttacacat tccctccttg    480
a                                                                     481

<210> SEQ ID NO 5
<211> LENGTH: 23
<212> TYPE: DNA
<213> ORGANISM: Artificial
<220> FEATURE:
<223> OTHER INFORMATION: oligonucleotide primer

<400> SEQUENCE: 5
ttgcatgcag ggttgctagc tag                                             23
```

```
<210> SEQ ID NO 6
<211> LENGTH: 23
<212> TYPE: DNA
<213> ORGANISM: Artificial
<220> FEATURE:
<223> OTHER INFORMATION: oligonucleotide primer

<400> SEQUENCE: 6
gaagatatag caccgtgtca gac                                          23

<210> SEQ ID NO 7
<211> LENGTH: 23
<212> TYPE: DNA
<213> ORGANISM: Artificial
<220> FEATURE:
<223> OTHER INFORMATION: oligonucleotide primer

<400> SEQUENCE: 7
ggaaaagtaa cagggctgtg aag                                          23

<210> SEQ ID NO 8
<211> LENGTH: 23
<212> TYPE: DNA
<213> ORGANISM: Artificial
<220> FEATURE:
<223> OTHER INFORMATION: oligonucleotide primer

<400> SEQUENCE: 8
acaattgata tacagagctt tgg                                          23

<210> SEQ ID NO 9
<211> LENGTH: 23
<212> TYPE: DNA
<213> ORGANISM: Artificial
<220> FEATURE:
<223> OTHER INFORMATION: oligonucleotide primer

<400> SEQUENCE: 9
agaagttgct gggatacggt gtc                                          23

<210> SEQ ID NO 10
<211> LENGTH: 23
<212> TYPE: DNA
<213> ORGANISM: Artificial
<220> FEATURE:
<223> OTHER INFORMATION: oligonucleotide primer

<400> SEQUENCE: 10
atcgagcagt tccacgacgt gac                                          23

<210> SEQ ID NO 11
<211> LENGTH: 23
<212> TYPE: DNA
<213> ORGANISM: Artificial
<220> FEATURE:
<223> OTHER INFORMATION: oligonucleotide primer

<400> SEQUENCE: 11
cactgggcga cacggcactt gtc                                          23

<210> SEQ ID NO 12
<211> LENGTH: 23
<212> TYPE: DNA
<213> ORGANISM: Artificial
<220> FEATURE:
<223> OTHER INFORMATION: oligonucleotide primer
```

```
<400> SEQUENCE: 12
gacgacgatg gcgttcgacg aag                                              23

<210> SEQ ID NO 13
<211> LENGTH: 23
<212> TYPE: DNA
<213> ORGANISM: Artificial
<220> FEATURE:
<223> OTHER INFORMATION: oligonucleotide primer

<400> SEQUENCE: 13
ctacaaagcc atgaccacga gtg                                              23

<210> SEQ ID NO 14
<211> LENGTH: 23
<212> TYPE: DNA
<213> ORGANISM: Artificial
<220> FEATURE:
<223> OTHER INFORMATION: oligonucleotide primer

<400> SEQUENCE: 14
ggtgctcctt cttcttctat ctc                                              23

<210> SEQ ID NO 15
<211> LENGTH: 27
<212> TYPE: DNA
<213> ORGANISM: Artificial
<220> FEATURE:
<223> OTHER INFORMATION: oligonucleotide primer

<400> SEQUENCE: 15
caccagaaga agaaggagca ccaatac                                          27
```